United States Patent
Scaife

(10) Patent No.: US 10,758,853 B2
(45) Date of Patent: Sep. 1, 2020

(54) COMBINED BRIQUETTING AND CYCLONIC SEPARATION DEVICE AND PROCESS CAPABLE OF REMOVING PARTICLES FROM A FLUID STREAM AND CONVERTING DIRECTLY INTO BRIQUETTES

(71) Applicant: MOBIAIR PTE. LTD., Amazana (SG)

(72) Inventor: Martin Scaife, Singapore (SG)

(73) Assignee: MOBIAIR PTE. LTD., Amazana (SG)

( * ) Notice: Subject to any disclaimer, the term of this patent is extended or adjusted under 35 U.S.C. 154(b) by 213 days.

(21) Appl. No.: 15/881,599

(22) Filed: Jan. 26, 2018

(65) Prior Publication Data
US 2018/0147516 A1  May 31, 2018

Related U.S. Application Data

(63) Continuation of application No. PCT/SG2016/050368, filed on Jul. 29, 2016.

(30) Foreign Application Priority Data

Aug. 2, 2015  (SG) ............................. 10201506050T

(51) Int. Cl.
*B01D 45/12*  (2006.01)
*B01D 45/18*  (2006.01)
(Continued)

(52) U.S. Cl.
CPC ........ *B01D 45/18* (2013.01); *A61F 13/15617* (2013.01); *B01D 45/12* (2013.01);
(Continued)

(58) Field of Classification Search
CPC ........ B01D 45/18; B01D 45/12; B01D 45/16; B01D 46/0086; B01D 46/0005;
(Continued)

(56) References Cited

U.S. PATENT DOCUMENTS

| 3,441,387 A | * | 4/1969 | Dye | .......................... B01J 2/22 23/313 R |
| 4,128,404 A | | 12/1978 | Stamatiou et al. | |
| 4,695,299 A | * | 9/1987 | Spadaro | ................. B01D 46/12 55/315 |
| 2005/0252179 A1 | * | 11/2005 | Oh | ........................ A47L 9/1625 55/337 |
| 2006/0112617 A1 | | 6/2006 | Clark et al. | |
| 2007/0084160 A1 | * | 4/2007 | Kim | ........................ A47L 5/28 55/345 |

(Continued)

FOREIGN PATENT DOCUMENTS

| CN | 2086751 | 10/1991 |
| CN | 104368218 | 2/2015 |

(Continued)

*Primary Examiner* — Dung H Bui
(74) *Attorney, Agent, or Firm* — Peacock Law P.C.; Janeen Vilven

(57) ABSTRACT

Process and apparatus capable to remove particles from a fluid stream (such as air or water) and directly convert the removed particles into a solid compact format commonly known as briquettes in a standalone combined single unit operation. The outlined process and equipment operates without the need for rotary valve technology and uses air versus hydraulics offering a cost competitive equipment solution for the end user. Active processes within the apparatus actively control the dust thereby allowing a variety of particles to be processes irrespective of moisture content and surface adhesive characteristics. Having the low-cost capability to convert explosive air/dust mixtures into briquettes significantly enhances safety and also reduces the associated manhandling effort required with disposing of collected dust with many briquettes typically having 100-500× the density of the incoming particles. In many regions the produced briquettes have a second hand value thereby creating a value stream from a zero value dust stream.

12 Claims, 18 Drawing Sheets

(51) Int. Cl.
*A61F 13/15* (2006.01)
*B01D 45/16* (2006.01)
*B01D 46/00* (2006.01)
*B01D 46/10* (2006.01)
*B01D 46/42* (2006.01)
*F24F 11/39* (2018.01)

(52) U.S. Cl.
CPC .......... *B01D 45/16* (2013.01); *B01D 46/0005* (2013.01); *B01D 46/0086* (2013.01); *B01D 46/10* (2013.01); *B01D 46/4254* (2013.01); *F24F 11/39* (2018.01)

(58) Field of Classification Search
CPC ................ B01D 46/10; B01D 46/4254; A61F 13/15617; F24F 11/39
See application file for complete search history.

(56) References Cited

U.S. PATENT DOCUMENTS

| | | | |
|---|---|---|---|
| 2010/0115727 A1* | 5/2010 | Oh | A47L 9/1625 15/347 |
| 2011/0140298 A1* | 6/2011 | Politi | A61K 9/2095 264/121 |
| 2011/0220745 A1 | 9/2011 | Politi | |
| 2014/0059800 A1* | 3/2014 | Bassett | A47L 9/0072 15/353 |

FOREIGN PATENT DOCUMENTS

| | | |
|---|---|---|
| RU | 2531313 | 10/2014 |
| WO | 2009/135946 | 11/2009 |
| WO | 2017/023205 | 2/2017 |

\* cited by examiner

COMBINED BRIQUETTING AND CYCLONIC SEPARATION DEVICE AND PROCESS CAPABLE OF REMOVING PARTICLES FROM A FLUID STREAM AND CONVERTING DIRECTLY INTO BRIQUETTES

CROSS-REFERENCE TO RELATED APPLICATIONS

This application is a continuation application of International Patent Application PCT/SG2016/050368, filed Jul. 29, 2016, which claims priority to and the benefit of the filing of Singapore Patent Application No. 10201506050T, filed on Aug. 2, 2015, and the specification and claims thereof are incorporated herein by reference.

BACKGROUND OF THE INVENTION

Field of the Invention (Technical Field)

The present invention outlines new apparatus and process solutions capable to remove particles from a fluid stream (such as gaseous fluids like air or liquid fluids like water) and convert the removed particles directly into a solid compact format commonly known as briquettes. Particles are removed from the fluid stream via a cyclonic separation process and are fed directly or indirectly via pre-compaction and transportation processes into an integrated briquetting device that compacts the collected material for ease of collection and enhanced transportation efficiencies. The present invention is particularly suitable to treat particle loaded air streams in manufacturing sites for hygiene products, such as feminine hygiene pads, napkins, pet pads, bed pads, baby and adult diaper, such that the particles may be pulp, sand, Superabsorbent Polymer (SAP) particles, or pulp or synthetic fibers or dust. Actively controlling the dust between the cyclonic separation process and briquetting process allows a variety of particles to be reliably processed including sticky materials such as SAP particles being transported in a moist air stream. Converting the dust into a compressed briquette form as early as possible in any production process enhances safety as air/dust mixtures are extremely explosive and even settled non-airborne dust is a safety risk as it may fuel secondary explosion events. The combination of both apparatus and processes forms a totally functioning overall apparatus and process without the need for incumbent rotary valve technology that is commonly installed on cyclonic separation equipment. It provides a low-cost solution as it operates without hydraulic technology, as presently typically employed for briquetting, thusly allowing low cost manufacture of the apparatus. End users can therefore site this new compact low-cost apparatus close to the dust extract point ensuring minimal ductwork requirements and minimal pressure loss in the associated ductwork.

Many operators of production sites that produce dust (such as dust sand, fibers, saw dust etc.) wish to take dust directly from their process and process it directly with a cyclonic separation process. To this end, a particle loaded fluid stream is submitted to a cleaning step, such as s filter process step, for which drum filter or corrugated disc filter technology may be employed, requiring a media cleaning device that removes the dust in concentrated form from the drum or corrugated disc. This airflow stream with an increased particle concentration must be cleaned and the respective high particle or dust levels removed. It must also be noted that the present invention is applicable to particle loaded fluid streams in general, and thusly may be applied to treating particle loaded liquid, e.g. aqueous, fluids or gaseous fluids, e.g. air.

To clean these contaminated fluid streams, two commonly used technologies exist to do this, either by (i) filtration systems using sock/cartridge filter systems or (ii) cyclonic separation. Both technologies offer functional methods to remove the dust from an air stream with a high particle load, however both of these processes are far from ideal.

Filtration technology such as sock/cartridge filter systems are not ideal as the dust is not compressed into a dense format and as such, by default, due to the low density and high volume of the removed dust requires continuous supervision by operators who must collect the dust on frequent regular intervals. This sock/cartridge filter system is also not the best solution in terms of safety as the very high levels of air-borne dust in the process increase the fuel levels for a potential air/dust explosion (initial explosion). Further, settled dust within the filter system, such as dust collected in the cartridge or within the sock, can become air-borne during an initial explosion and fuel subsequent secondary explosion events which are in most instances more catastrophic than the initial explosion. Of further concern, any lapse in the filter cleaning or replacement process or a blocking of the filter media cause the media cleaning process, such as a nozzle cleaning process to fail which subsequently causes the air stream to reach concentrations between the lower explosive limit (LEL) and the upper explosive limit (UEL). Such an event combined with an ignition source (such as nut, bolt or shim entering a process fan and creating a spark) has the potential do destroy a complete factory with many such instances having occurred to date.

Cyclonic separation devices take a fluid stream (such as air or water) consisting of particles requiring removal from this fluid stream via a different process concept. In the cyclonic separation process the fluid stream is rotating within the cyclone in a vortex style flow, this flow thereby creating a centrifugal force on the fluid stream with the particles such that the heavier particles are forced to the outside of the vortex upon which they come in contact with the side walls of the cyclone, loose velocity and fall out of the vortex by gravity. Upon exiting the vortex, the particles today typically fall into a rotary valve that prevents airflow in and out of the lower section of the cyclone that disturbs the vortex within the cyclonic process, and once the valve has rotated, the dust free-falls by gravity from the rotary valve. From this point onwards, the dust may be collected in bags, or may be sent to a briquetting system. Collecting the dust in bags is considered somewhat better than sock/cartridge filter technology as the bag is not used as a filter medium and fine dust cannot penetrate the sock filter media, however, the dust is still collected in a non-dense format requiring high manpower requirements to replace and creating a safety risk due the explosive nature of air/dust explosions.

To eliminate these problems, many cyclone installations feed their dust from the rotary valve into the in feed hopper of a briquetting system. The combination of the cyclone and the briquetting device has been relatively successful over the past years as this solves the high labour issues as well as significantly reduces or even eliminates all initial and secondary explosion event risks.

Despite the combination of cyclonic separation and briquetting systems being the preferred solution on most installations, the overall integration of the equipment within the respective factory is not ideal.

Briquetting machines are typically very expensive, with any good quality system costing often over 100 000 US-Dollar, the cost partially due to the high pressures involved and the hydraulic system required to achieve this force. With such a high capital cost using one briquetting machine for every cyclone would be too cost prohibitive. As such, the typical solution for this is to group multiple cyclones together and have two or more cyclonic systems discharging into one briquetting device.

It should be noted that the term "briquetting" or related ones are used in the present context to relate to any active compacting of low density matter, i.e. an accumulation of particles, to a significantly higher density, e.g. if the accumulated matter exhibits an average density of below 100 kg/m$^3$, the resulting briquettes exhibit a statistically significantly higher density. As such, "briquetting", "briquettes", "briquetter" also encompass equivalent terms, such as "pelletizing", . . . , "compacting", "press agglomerating", . . . . For most purposes, a higher density is preferable, and thus may reach more than 50 kg/m$^3$, often more than 100 kg/m$^3$ or even well over 300 kg/m$^3$. Typically, though not necessarily, the compacting process creates sufficient adherence between the particles, and if not, compacting aids may be added. The briquettes may exhibit a size of less than 125 000 cm$^3$, often less than 1000 cm$^3$, or even less than 1 cm$^3$, but typically more than 0.001 cm$^3$, or often more than 0.008 cm$^3$.

In principle, from a separation point of view, the use of more cyclones is better, however, another process restriction becomes important, namely the fluid speeds in the duct system. The fluid flow volumes to clean the filter media are typically very low, and are typically far less than 10% of the total fluid flow passing through the filter system. Considering a particle loaded air stream, air speeds within the duct transporting the particle loaded air typically must be more than about 15 m/sec or higher keep the particles suspended, the duct diameter is typically quite small. For instance, duct diameters on the nozzle cleaning duct entering the cyclone on production systems used to make baby diapers is only about 100 mm in diameter. Transporting air at speeds over 15 m/sec in a duct of only 100 mm in diameter creates large pressure drops to occur which can only be overcome by installing additional process fans in series along the duct length. Also of consideration, creating a turbulent airflow within the duct system is detrimental to the subsequent cyclone air separation process and as such, the use of multiple curved ducts prior to the cyclone air separation process it typically avoided.

As a result of this "pressure drop" process effect, cyclonic separation equipment is typically located close to the filtration process and as such, installations in factories where filters are located far apart typically do not group multiple cyclones together. Within the hygiene sector where line spacing (distance between production lines) can range from 6-20 m, grouped cyclone configurations typically range from only two to four units.

A new combined low-cost briquetting and cyclonic separation device would have many advantages such as in that the device could be located close to the filter, thereby not requiring long duct runs of lower diameter duct. The combination of the two technologies also mean that usual rotary valve technology, that is typically not a reliable robust process do to blocking issues and high maintenance issues, can be fully eliminated.

Furthermore, if the briquetting device also actively controls and feeds the dust from the cyclonic separation process into the briquetting and not rely on gravity to move the dust, the risk of blocking and other related issues could be completely eliminated and furthermore, SAP being transported in a moist air stream (such as factories operating without HVAC) can also be reliably processed.

In RU2531313C1, it is described to collect dust in a cyclone, add coagulating liquid in the lower part thereof, feeding the mixture to roller press underneath the cyclone, forming briquettes, and loading these briquettes to a collecting hopper. US2006/0155281 describes briquetting of coal particles including a pre-compaction step comprising a pre-compaction screw followed by a nip compaction between two rolls. WO2009/135946 as well as WO2008/056021 by same applicant describe granulation for tablets by means of a roller compactor. CN2086751U (see also translation by Espacenet) is concerned with a compacting step involving a spiral compacting device.

SUMMARY OF THE INVENTION

A first objective of the present invention is to directly connect a briquetting device with cyclonic separation device preferably in combination with particular connection technology to connect the briquetting device with the cyclonic separation device, thusly providing new low-cost methodologies for the manufacture of equipment, optionally of additional ancillary equipment such as safety and process monitoring equipment. The combination of both technologies eliminates conventional rotary valve technology and active control methodologies can be used to ensure reliable and consistent transportation of particles without blocking.

Further, the present invention provides an active transportation technology, rather than gravity drive free-flow, used to transport the dust from the outlet of the cyclonic process into the inlet of the briquetting device concurrently with a one or more pre-compaction process(es).

To achieve a cost competitive equipment solution, the use of hydraulic compaction systems is often cost prohibitive and as such the use thereof needs to be minimized, if not eliminated, to provide attractive business proposition to the end-user installing this technology. An alternative to such hydraulic compaction systems would be the use of compressed air, however most production sites operate an air pressure system with 90 PSI (620 kPa) air pressure, which is not sufficient to create the required to make good quality densely formed briquettes. Thus, the present invention relates to multi-stage air cylinders and their use to attain the higher compression forces required.

Further embodiments of this invention relate to modifying the routing of the incoming cyclonic airflow to provide a stepped position at the top section of the cyclone within which video camera surveillance technology and lighting systems can be installed as well as additional sensing system to monitor the cyclonic process within the cyclone.

A low cost, reliable combined briquetting device with cyclonic separation device thereby offers multiple benefits to the end-user in that (i) reduced man-effort requirements (ii) enhanced safety, (iii) reduced energy requirements as a result of the shorter ducting, (iv) low capital cost versus todays incumbent briquetting technology, (v) an easily expandable system allowing production sites to increase output by increases production line by production line without have limitations due to shared briquetting devices.

Thus, the present invention is a process and respective equipment to execute such a process, in particular a cyclonic separation process where the out-feed connects directly to a briquetting device, with one or more material pre-compaction steps prior to the final briquetting process. Preferably, the pre-compaction devices act simultaneously as transporting means for the particles towards the final briquetting device. Preferably, the pre-compaction means comprises a moving cylinder, preferably a multistage cylinder, such as between two and two million stages, driven by pressurized air.

In another aspect, the cyclonic separation process, wherein the out-feed connects directly to a briquetting device where material pre-compaction zones exist prior to the final briquetting process where one or more of these processes are housed within an airtight housing. Optionally, a pressure sensor to detect pressure differentials may be included in the airtight housing.

In a particular execution, the diameter of the initial cyclonic separator is smaller than the diameter in the later stages of the cyclonic separator, along the vortex flow path. Optionally, the difference in diameters is adapted to house a camera optionally further comprising an air jet positioned on the lenses of the camera preventing contamination build-up on the camera lens. Optionally, the difference in diameter is adapted to house a lighting system, or one or more sensing system(s) to detect blockages or material amounts within the cyclone, or the level of particles collected at the outlet of the cyclone.

In another aspect, the present invention is an equipment for separating particles from a fluid stream and briquetting the particles, which comprises:
  a cyclonic separator for accumulating particles of the particle loaded fluid in a particle outlet zone;
  a particle compactor for forming briquettes comprising at least one, optionally more, pre-compaction means and a final briquetting means, whereby the particle compactor is essentially unitary with the cyclonic device by being directly connected thereto, preferably directly underneath along the direction of gravity.

The particle compactor may be a mechanically compactor, an air-pressure actuated compactor, more preferably comprising two or more stages, which preferably is low-pressure actuated, more preferably by air pressurized to less than 10 bar.

The cyclonic separator and at least a pre-compaction means are in an air-tight closed housing, optionally comprising a pressure sensor. The cyclonic separator may comprise a first zone and at least one further zone, wherein the cyclone exhibits in the first zone a diameter that is smaller than the one in the further zone, and the cyclone housing may exhibit a step between the first and further zone as a result of the differing diameters. In a preferred execution, a sensing means to allow surveillance and control of the cyclonic separator may be positioned into this step in the cyclone housing, between the first and a further zone. The sensing means may comprise one or more elements selected from the group consisting of
  a camera system,
  a lighting system,
  a cleaning air jet system,
  a material mass detection system,
  a material accumulation detection system.

In yet another aspect the present invention is a manufacturing set up that comprises such an equipment for separating particles from a fluid stream and briquetting the particles, and which may further comprise an automated briquette transport system, preferably a continuous transport system, preferably selected from the group consisting of:
  Screw conveyor;
  Belt conveyor;
  bucket conveyor,
  Pneumatic transfer conveyor;
  Vibrating conveyors;
  Continuous flow conveyors.

Further, the manufacturing equipment may further comprise a briquette storage or disposal system selected from the group consisting of
  Bags, preferably big bags exhibiting a volume of 100 l preferably of 1 m$^3$ or more;
  Drums, preferably moveable drums;
  Silos preferably exhibiting a volume of more than 1 m$^3$;
  Storage space adapted to allow heaps of briquettes being formed, preferably heaps exhibiting a volume of 1 m$^3$, more preferably more than 10 m$^3$;
  A continuous transport system connected to a downstream processing step, preferably selected from the group consisting of thermal recuperation and waste treatment system.

In yet another aspect, the present invention is a process for separating particles from a fluid stream and briquetting the particles, comprising the steps of
  providing
    a stream of particle loaded liquid or gaseous fluid,
    a cyclonic separator for accumulating particles of the particle loaded fluid stream in a particle outlet zone,
    a particle compactor for forming briquettes comprising at least one, optionally more pre-compaction apparatus and a final briquetting apparatus;
  feeding the stream of particle loaded fluid into the cyclonic separator;
  accumulating particles in the particle accumulating zone of the cyclonic separator;
  transferring the accumulated particles through an outlet zone of the cyclonic separator to the particle compactor;
  submitting the particles to a pre-compacting step;
  transferring the pre-compacted particles, optionally via one or more further pre-compacting steps, to the final briquetting step, preferably by employing no other transport means than the pre-compaction means;
  actuating the final briquetting means for forming the briquettes, preferably
    by an actuation means that concurrently drives the pre-compaction means, or
    by using pressurized gaseous fluid, preferably air, for actuating the actuation means, more preferably low pressure air, and even more preferably air under a pressure of less than 10 bar.

The particles may exhibit differing properties selected from the group consisting of composition, size, and density. In particular for the application in a manufacturing process of hygiene particles, the gaseous fluid may be air and particles may comprise particles selected from the groups consisting of cellulose fibers or dust and superabsorbent polymer particles. The briquettes may exhibit a size of less than 125 000 cm$^3$, preferably less than 1000 cm$^3$, more preferably less than 1 cm$^3$ but preferably more than 0.001 cm$^3$, more preferably more than 0.008 cm$^3$. They may further exhibit a density of more than 100 kg/m$^3$, preferably more than 800 kg/m$^3$, and even more preferably more than 1000 kg/m$^3$.

The process may comprise additional process steps, such as
  Providing an automated briquette transport system, preferably a continuous transport system, preferably selected from the group consisting of
    Screw conveyor,
    Belt conveyor, Bucket conveyor,
Pneumatic transfer conveyor,
Vibrating conveyor,
Continuous flow conveyors;
Providing a briquette storage or disposal system preferably selected from the group consisting of
Bags, preferably big bags exhibiting a volume of more than 100 l, preferably more than 1 m³,
Drums, preferably moveable drums;
Silos, preferably exhibiting a volume of more than 1 m³;
Storage space adapted to allow heaps of briquettes being formed, preferably heaps exhibiting a volume of 1 m³, more preferably more than 10 m³;
A continuous transport system connected to a downstream processing step, preferably selected from the group consisting of thermal recuperation and waste treatment system.
Transporting the briquettes by the transport system to the storage or disposal system.

BRIEF DESCRIPTION OF THE SEVERAL VIEWS OF THE DRAWINGS

Figures may not be to scale, and same numerals depict same or equivalent elements of features.

DETAILED DESCRIPTION OF THE INVENTION

Figure 1:
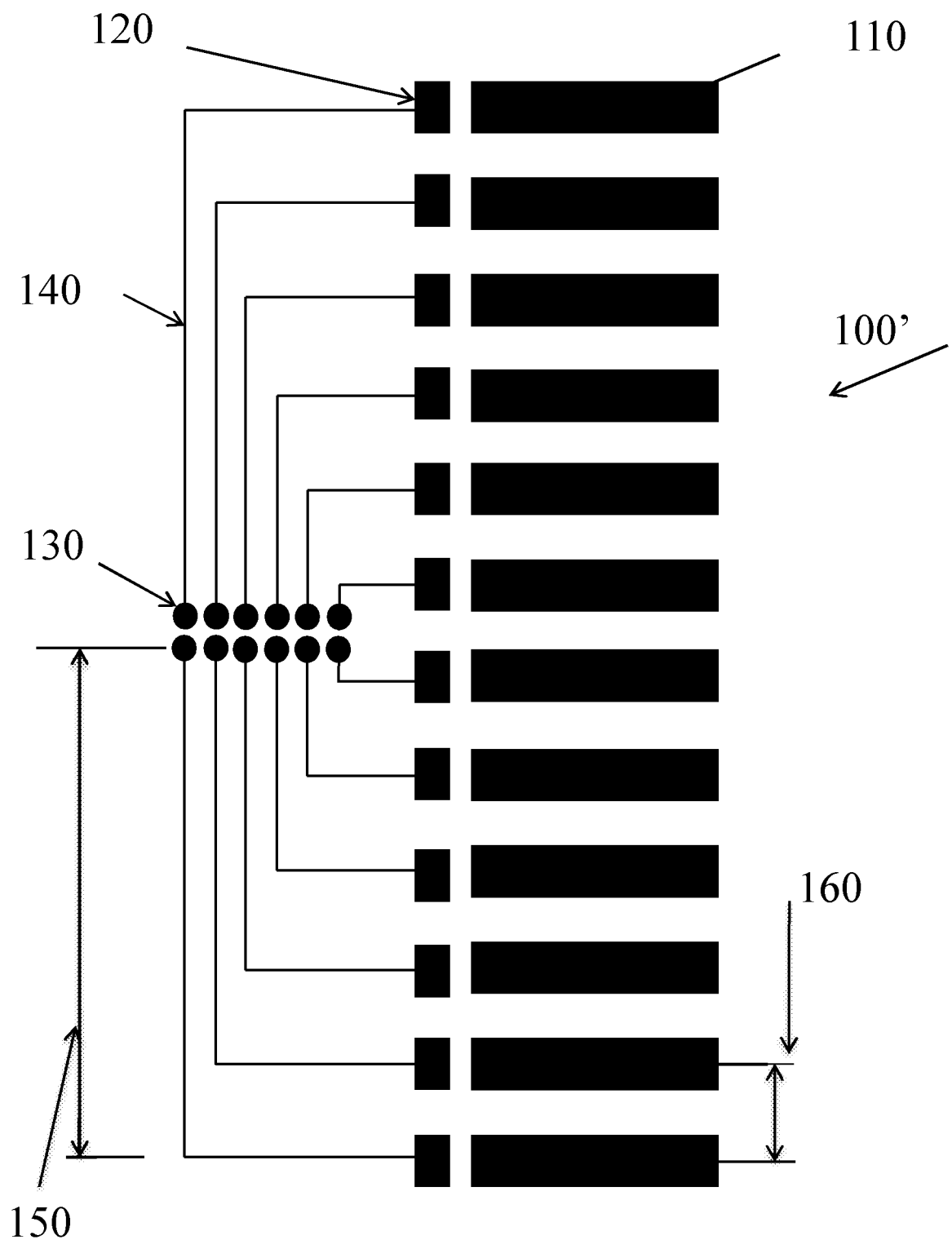
FIGS. 1 to 3 depict schematically a manufacturing set up of a production factory with various options to connect the dust generating equipment with dust treatment system.

The present invention relates to separating particles from a fluid stream and compacting of the separated particles in general, and as such is not particularly limited to the type of fluids (liquids or gaseous) or particles (minerals like sand, coal, organic matter like cellulose, synthetic materials like polymers, as primary particles or agglomerations or aggregates of such primary particles). The term "dust" includes all such particles that can become suspended in the fluid, e.g. air-borne in the case of air as fluid, but may then settle upon less movement of or agitation by the fluid. Most preferably, the present invention is applicable in a manufacturing environment with stationary production facilities that a create particle loaded fluid stream typically as an unwanted or undesired by-product. Many applications are in the field of cleaning air-born dust, and as such the explanation in the following also refers to such an application, though the skilled person will be able to readily apply the teachings herein to systems including other fluids, such as water, and the briquettes as may be formed in such a situation from the sludge exiting the cyclone may be further treated, such as being further dried.

However, for ease of explanation, but also because of a particularly well suited application, the following explanation of the present invention is made in the context of particle loaded air streams as may be generated in a manufacturing set-up as often seen in the manufacture of hygiene articles, such as—without intending any narrowing—diapers.

In many manufacturing sectors, cyclonic separation processes are typically preferred due to their simplicity and no need to contend with secondary filtration processes and filter media cleaning and replacement. And when a primary filtration process applies filter media, the cleaning of these may be suitably be achieved by air nozzle cleaning devices, thereby creating an air stream with relatively high particle loads, which can be very suitably be cleaned by cyclonic devices, preferably combined with briquetting. For any of these scenarios, converting the extracted dust into a compressed briquette form as early as possible in any production process enhances safety as air/dust mixtures are extremely explosive and even settled non-airborne dust is a safety risk as it fuels secondary explosion events. The combination of both apparatus and processes forms a totally functioning overall apparatus and process without the need for incumbent rotary valve technology that is commonly installed on cyclonic separation equipment.

However, as explained in the above, current briquetting implies high cost, and thus present manufacturing set-ups often aim at minimizing the number of compaction devices, such as by connecting particle loaded streams of several sources to one briquetting device.

Transporting particles within a fluid stream requires that the fluid stream(s) have a certain velocity. This velocity changes from fluid type to fluid type and particle type to particle type. Taking air as the fluid stream and SAP and pulp dust as the assumed particles, a robust transport process of the SAP and pulp dust particles typically occur at speeds above 15 meters per second. When for instance assuming a flow rate of 500 cubic meters per hour and a duct diameter of say 100 mm a sufficient air speed is achieved. Despite this being a functioning process, the energy losses in transporting air at these speeds are significant as the pressure drop across the low diameter 100 mm duct is significant. With such a process constraint, siting the SAP and pulp dust extraction equipment as close to the process as possible is preferred to ensure lowest on-going operating costs.

As indicated before, the concept of small duct size and briquetting do however not marry well together with current technology as the capital cost of briquetting technology is considerable thereby meaning that currently available briquetting equipment is only viable to install when multiple cyclones are feeding into a single briquetting device. Locating a number of cyclones in a single position typically means long ducting is required to connect the cyclone to the upstream process and here is where the large pressure drops are detrimental to this kind of installation.

FIG. 1 outlines generally a manufacturing set-up (100') where there are multiple production devices (110) for executing manufacturing processes requiring air that is filtered via a filtration device (120), as may be a drum or corrugated disc filter. The dust collected there can be cleaned with air nozzles and this concentrated air/dust mixture is transported with ducts (140) to cyclone separation devices (130) which feed into a common briquetting device (not shown). As the airflow volume may be small, e.g. 500 cubic meters per hour, a small duct diameter is required to achieve an adequate air speed within the duct to transport the dust from the production device to the cyclones. For the depicted scenario of each six manufacturing devices being symmetrically positioned relative to a cyclone battery, and a distance between neighboring production devices (160) of e.g. 15 m, a resulting maximum duct system length (150) is at least 85 m. As detailed in Example A herein below, the pressure drop in such a system may be about 15.5 inches of water (3869 Pa). This requires a vast amount of energy which adds significant cost to the factories on-going monthly electric bill.

Figure 2:
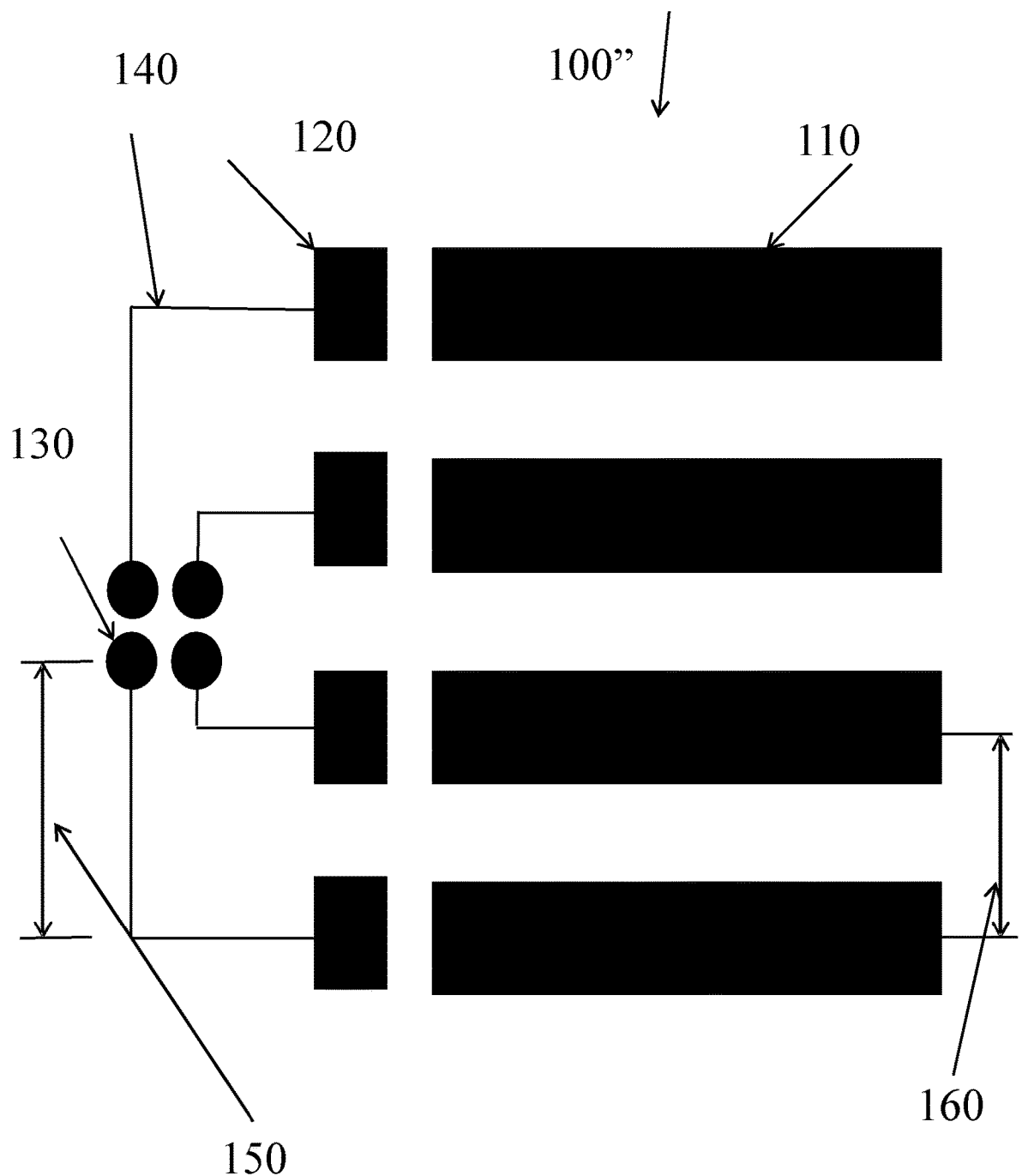

FIG. 2 depicts a similar scenario for the manufacturing set up (100"), however in this situation, the briquetting device is being fed by only 4 cyclones versus 12 cyclones as is depicted in FIG. 1. In this installation scenario, the maximum duct length is up to 20 m, and as detailed in Example B herein below, the resulting pressure drop of about 3.5 inches of water (888 Pa) is still high but far lower than in the scenario of FIG. 1.

Figure 3:
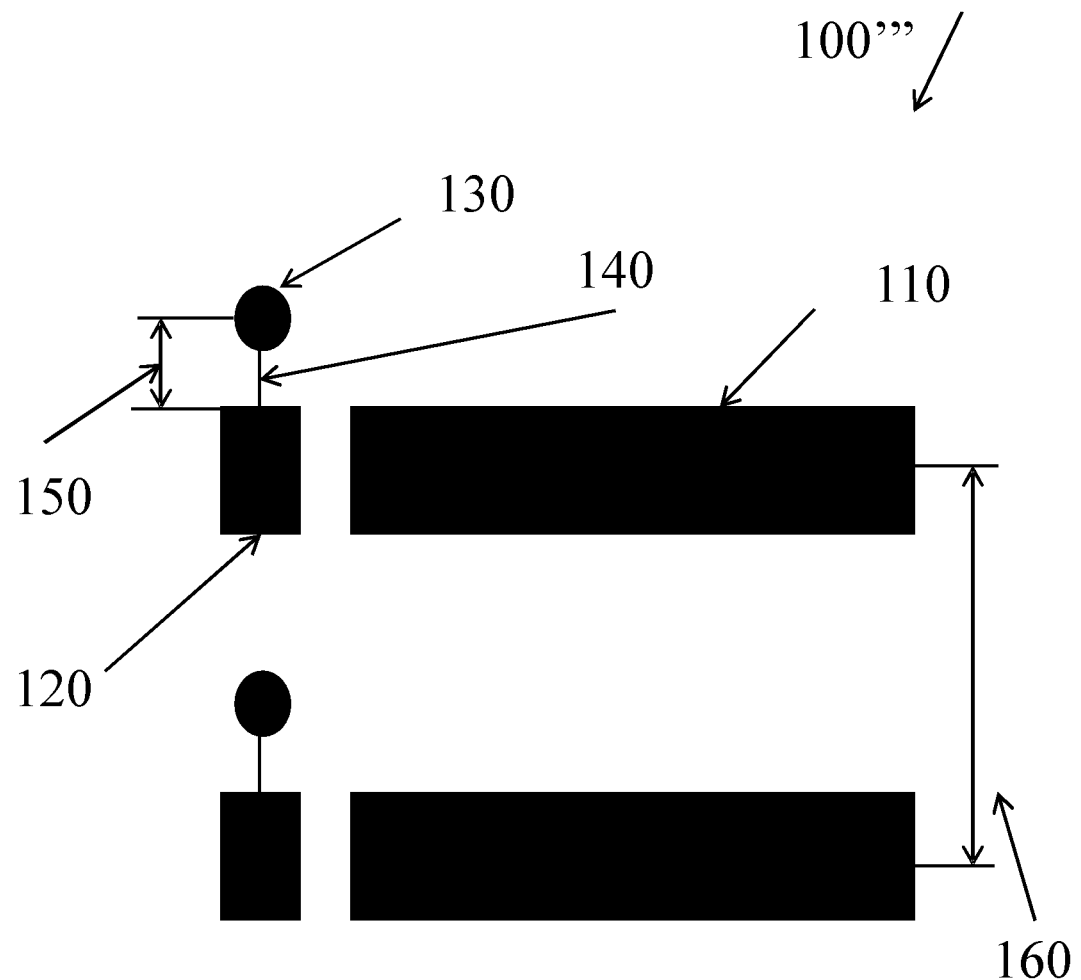

A far more preferred installation scenario for the manufacturing set up (100''') according to one aspect of the preset invention is outlined in FIG. 3 with only 2-meter duct length, resulting in a negligible pressure drop, see Example C herein below. When wanting to combine cyclonic separation with briquetting technology, it is therefore clear that positioning any cyclonic separation process as close to the up-stream source for the particle loaded fluid stream is critical to ensure lowest on-going energy costs. To date however, this has not been a viable option, as it requires a higher number of briquetting devices implying the high cost of conventional briquetting technology.

Figure 4A:
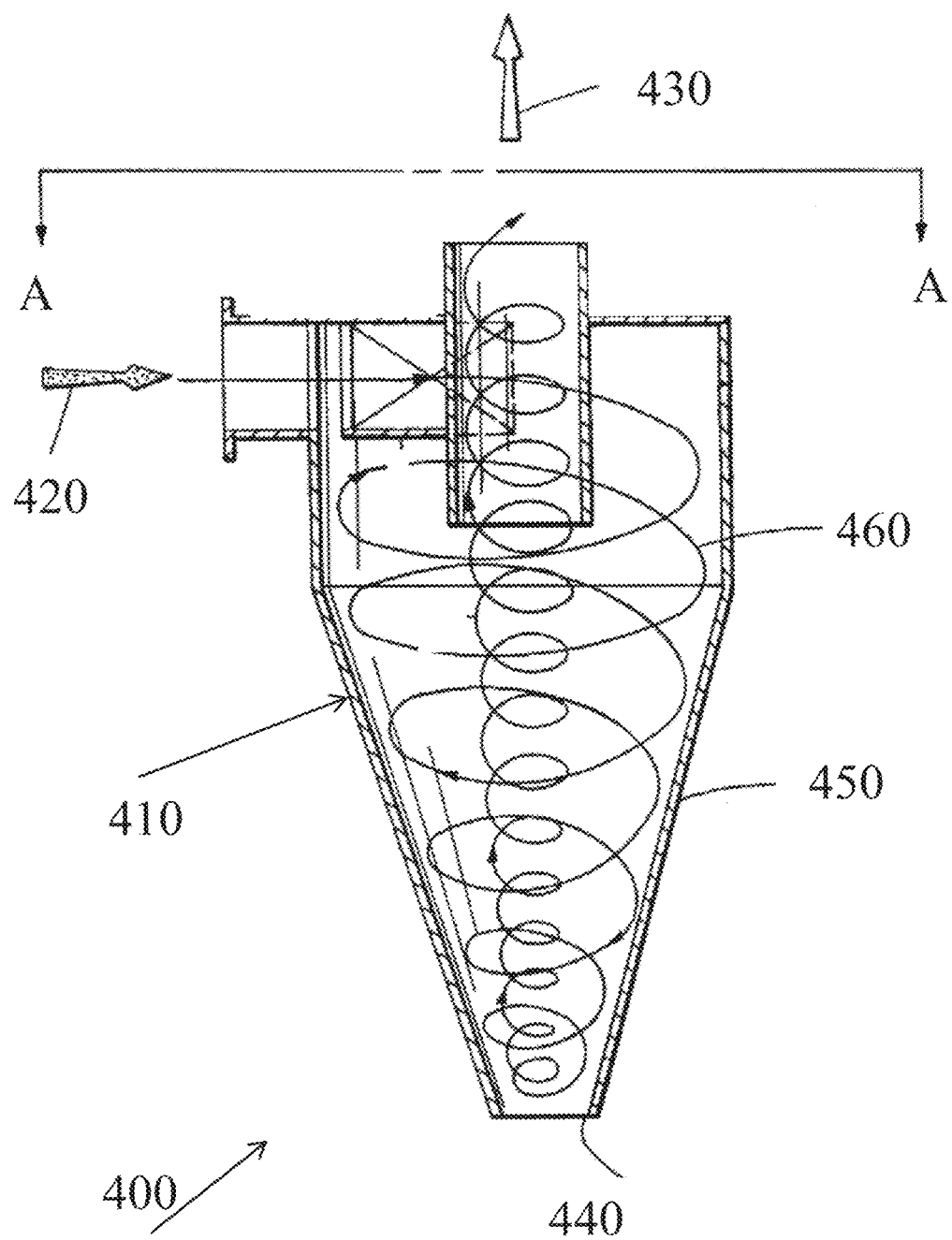
FIGS. 4A and B depict schematically a conventional cyclonic separation process.
Figure 4B:
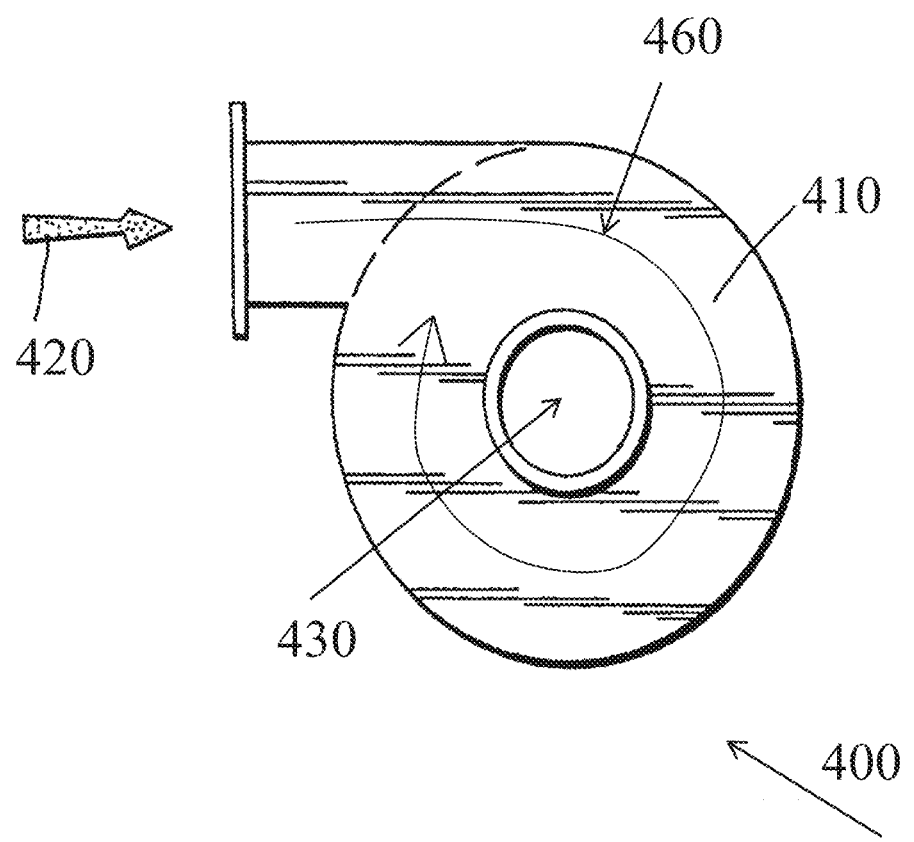

Going now in further detail in regard to cyclonic separation processes, FIGS. 4A and B depict an overview of a conventional cyclonic separation device (440) and the respective process where contaminated air (420) enters a cyclonic device (410) with clean air exiting at the top (430) and contaminants can be removed at the bottom (440). Air enters the cyclone and as a result of the in feed profile of the cyclone, the air is forced into a vortex formation as indicated in the figure (460). Heaver particles are forced to the outside of the cyclone thereby contacting the cyclone walls (450), thusly reducing in velocity and eventually accumulating or falling out of the cyclone at the bottom (440). FIG. 4B depicts the top view AA of the body of the cyclonic separation device (410) the incoming fluid contaminated, particle loaded stream (420) and the outgoing clean fluid stream (430). The vortex is indicated by a curved arrow (460).

Figure 5A:
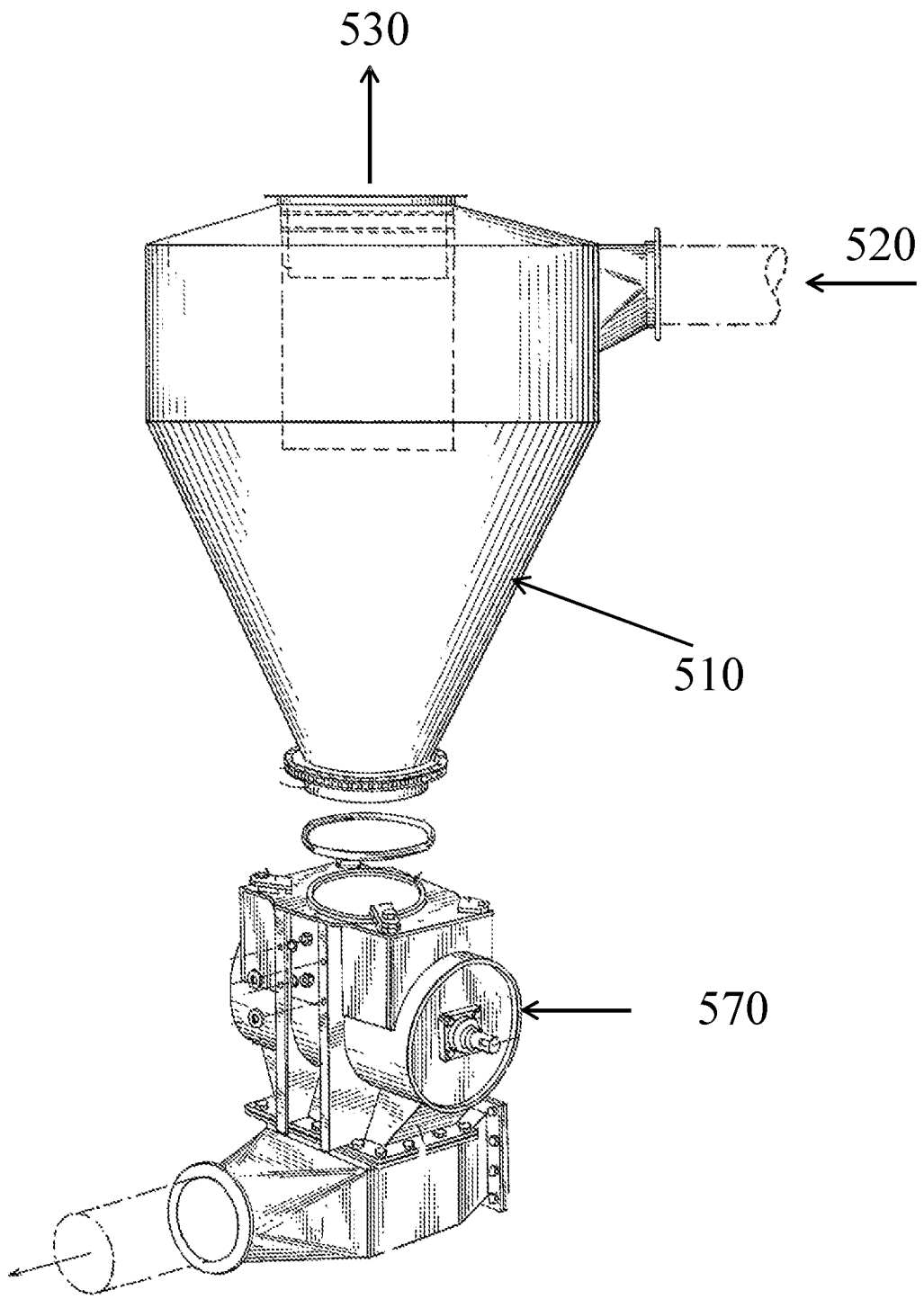
FIGS. 5A and B depict schematically a conventional cyclonic separation processes and a rotary valve assembly connected thereto.

When the particles exit the cyclonic separation processes they presently typically then move into a rotary valve system (570) at the outlet of the cyclone as depicted in further detail in FIGS. 5A and B. In conventional designs, this rotary valve is quite critical in the process in that the valve prevents air-flows going in and out of the cyclone and causing undesired balancing problems within the cyclone.

Particles falling from the bottom (540) of the cyclone (510) shown in FIG. 5A enter the rotary valve (590) via the rotary valve entry (580) and further fall into the pockets (585) of the rotary valve in the 12 o-clock position where they remain within these pockets until the pocket has rotated to the 6 o-clock position where the particles leave the rotary valve at exit (599), driven primarily by gravity. Due to relying on gravity, particles having any kind of a sticky surface, they will most likely not exit the pockets of the rotary valve and eventually the system will block. Other negatives exist in this process concept for the end-user in that for the value to be functioning, there must be an airtight seal between the rotary valve (590) and the rotary valve housing. This sealing is creating with the use of sealing bars (595) that must be positioned accurately to prevent excessive air loss. This increases maintenance and repairs costs for the end-user and also prevents certain types of material from being processed.

Figure 5B:
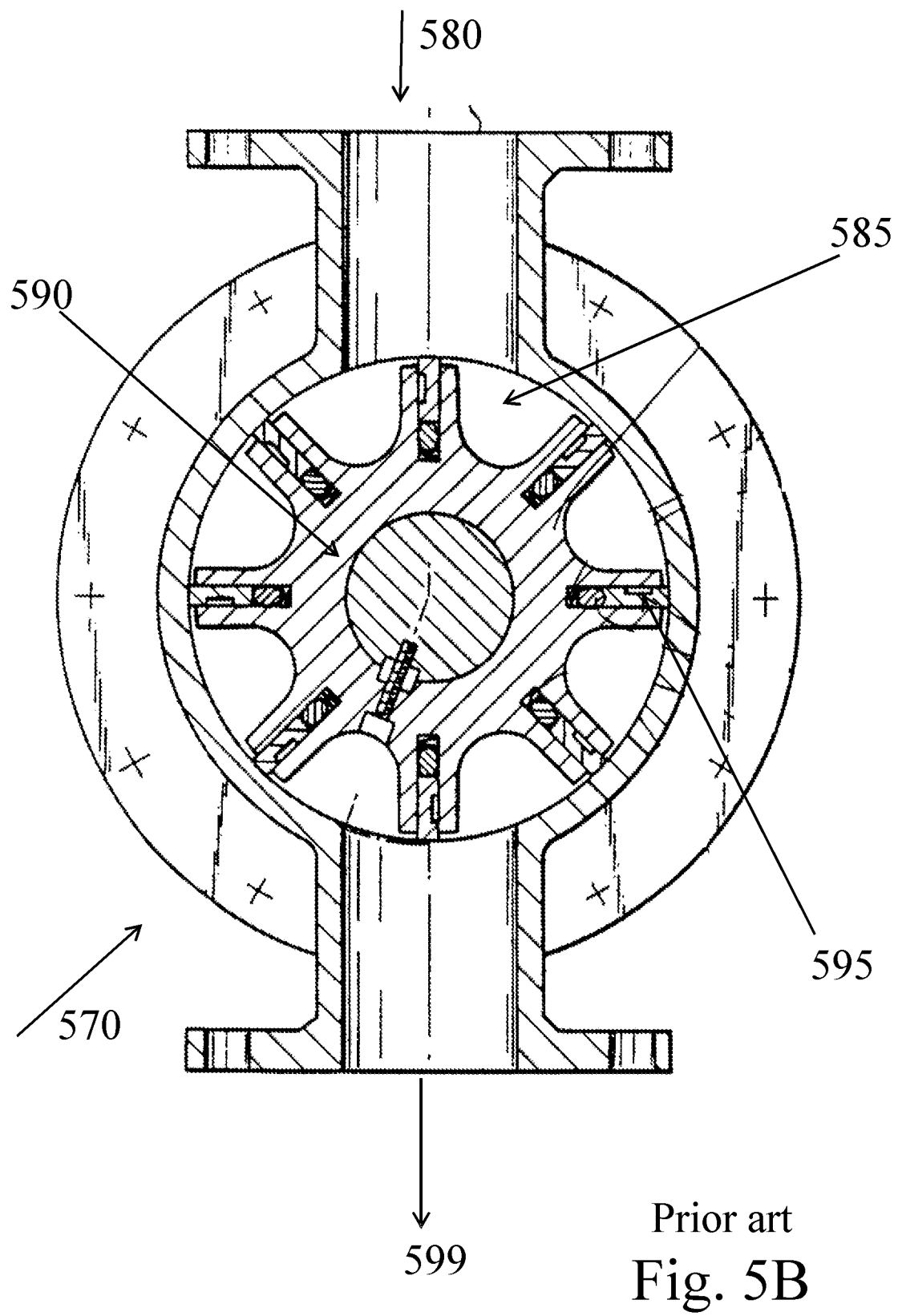
Figure 6A:
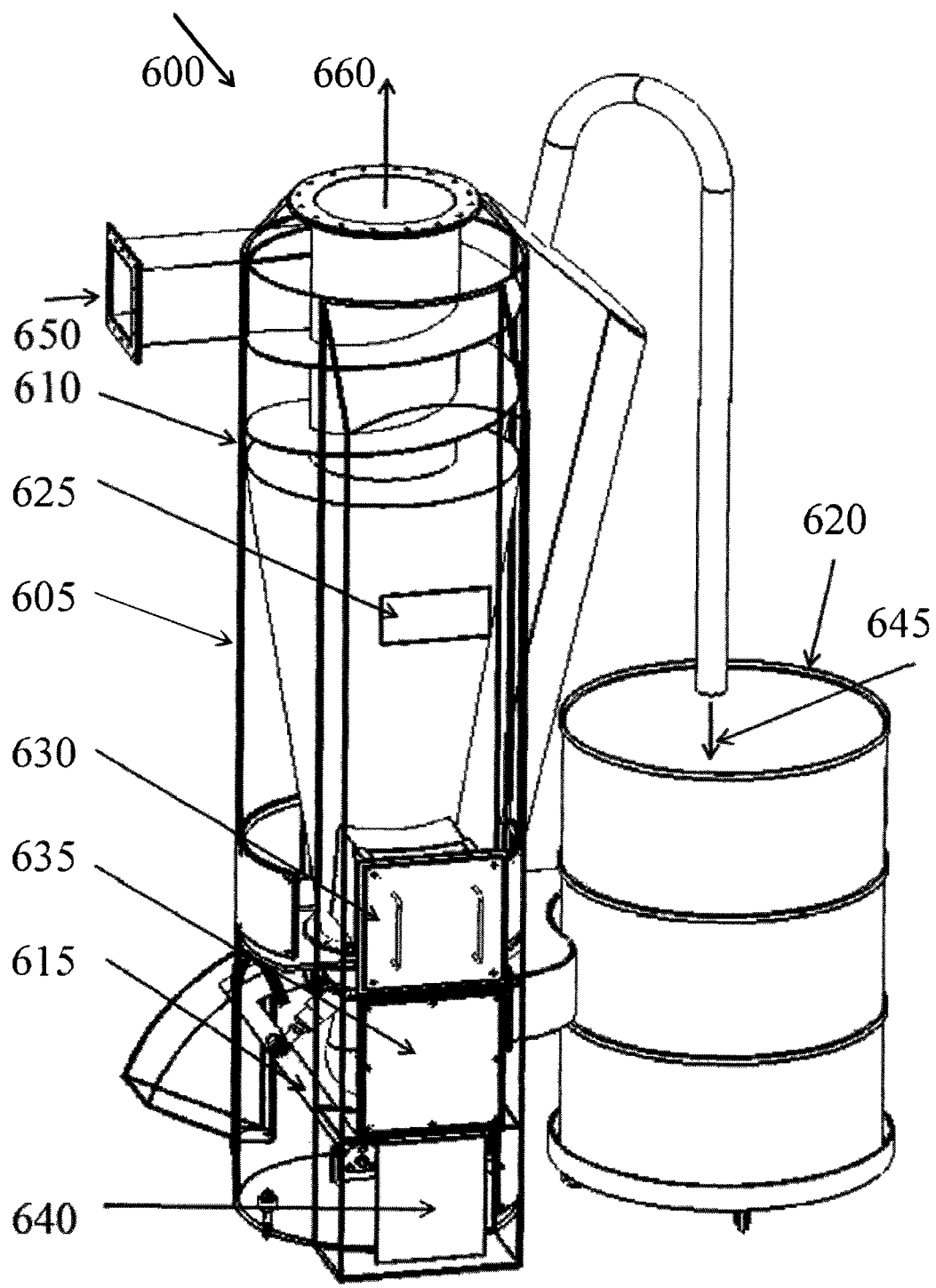
FIGS. 6A and B depict schematically a combined briquetting and cyclonic separation device suitable for the present invention.

A solution to solve the above-mentioned problems is depicted in FIGS. 6A and B. By integrating a low cost briquetting process directly to the cyclone, the rotary valve assembly as depicted in FIG. 5 can be completely eliminated. And by using air to operate the briquetting device, instead of hydraulics, the reduction in production costs allows the combined briquetting and cyclonic separation device to be installed close to the required filtration system thereby not requiring large energy costs to operate as the pressure drop within the ducting is very small.

FIGS. 6A and B depict schematically two views of an apparatus (600) where the out feed of a cyclone feeds into the briquetting process. As the processes between the out feed of the cyclone and the in feed of the briquetting process are essentially air tight, or close to being air tight, and air cannot pass through the briquetting process, the system has no requirements for a rotary valve. The apparatus comprises a machine body (605) with the cyclonic separation part or cyclonic separator (610) and the briquetting part or particle compactor (615). The contaminated incoming fluid stream (650) is entering radially into the cyclone entry zone, and the cleaned fluid stream (660) is leaving the cyclone via the central pipe. The compressed briquettes are collected via an out-feed pipe (645) into a collection system, here shown as a drum (620). Also depicted is a touch panel display (625) allowing to control the process conditions and settings. The cyclone may be accesses via a removable access hatch (630). Further indicated is an electrical cabinet (635) as well as an air systems cabinet (640).

Figure 6B:
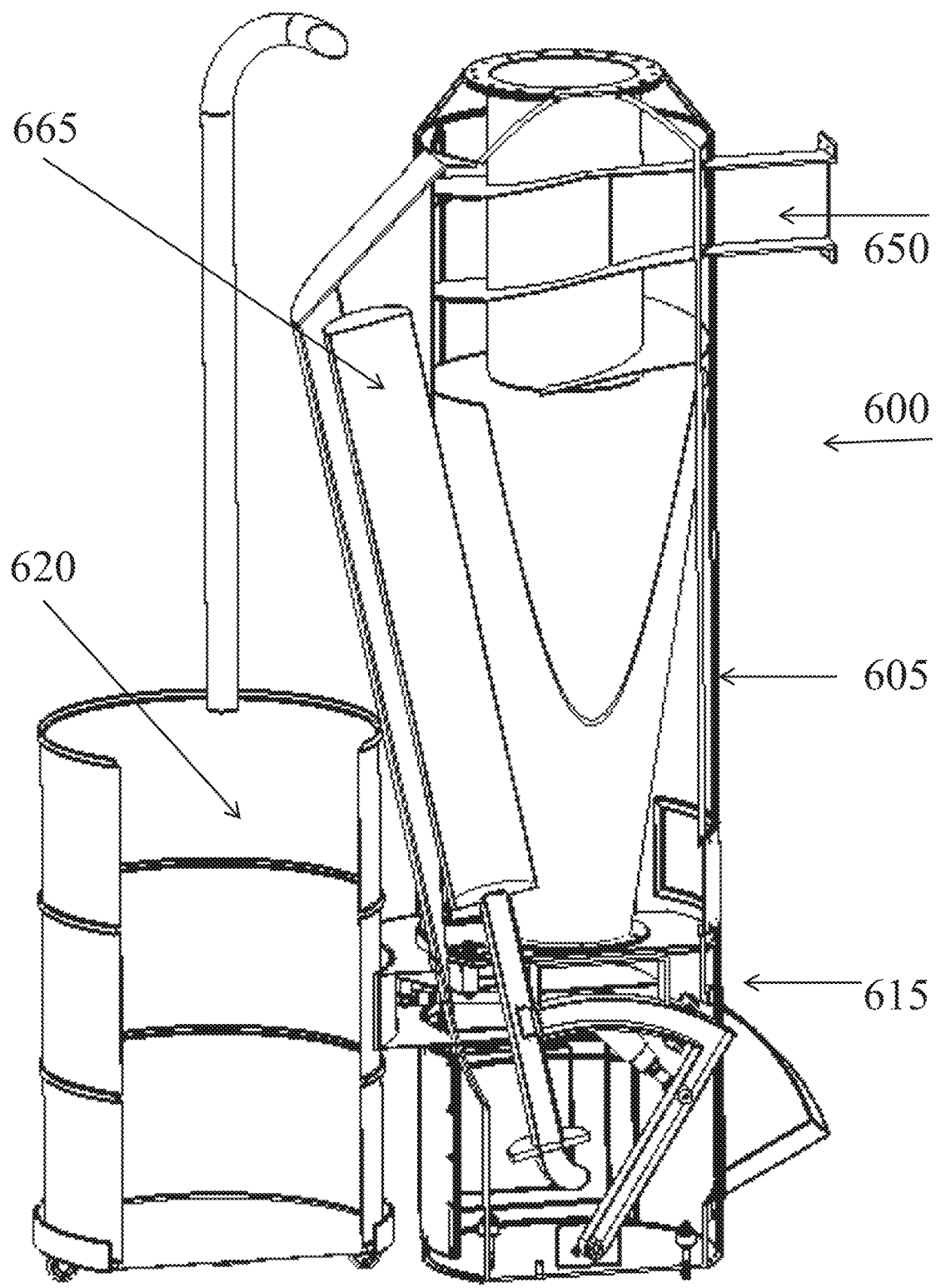
Figure 7:
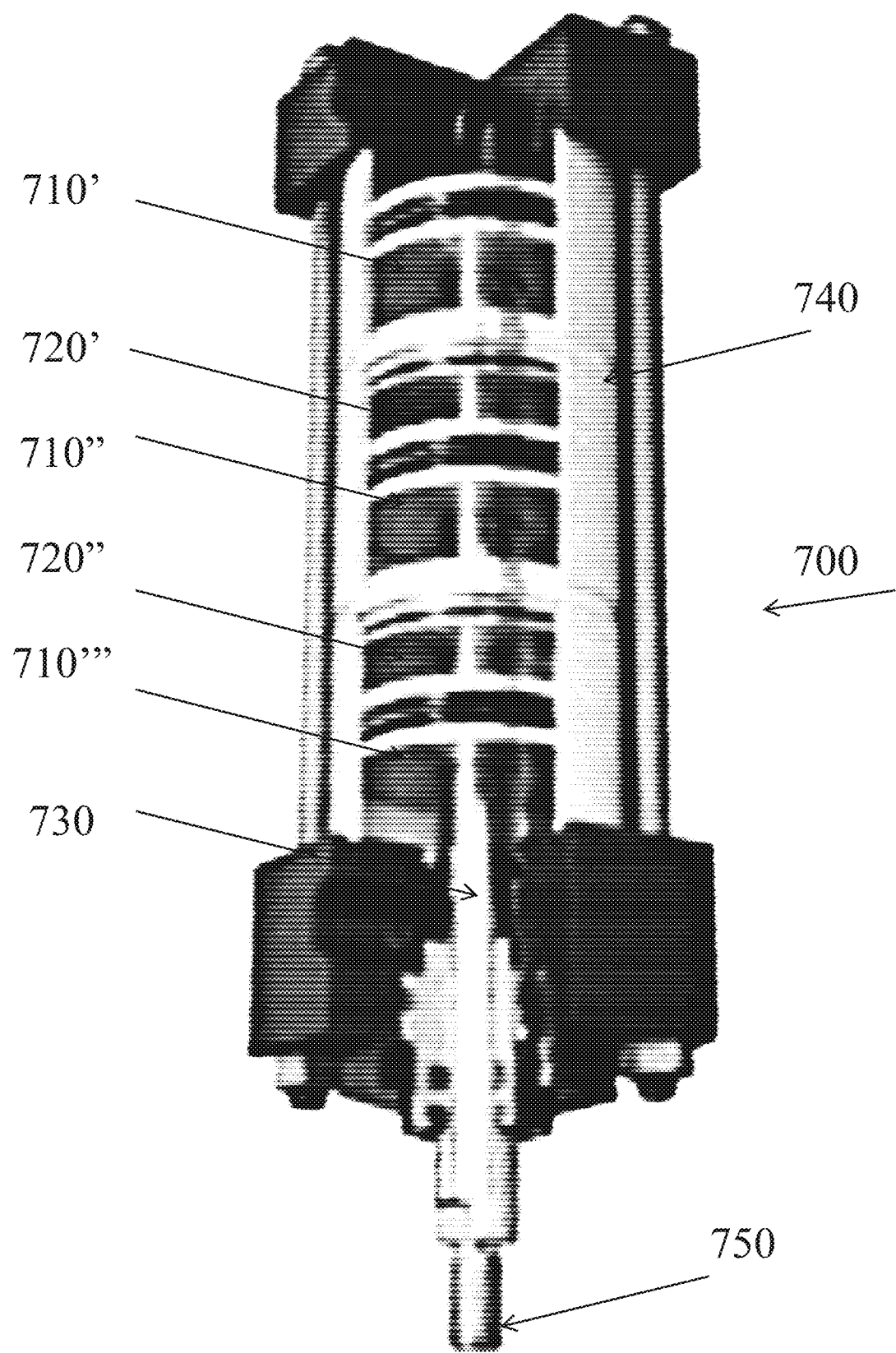
FIG. 7 depicts the multi stage air cylinder device suitable for the present invention.

Also shown in FIGS. 6A and 6B, the particle compactor (615) may be an air pressure actuate mechanical press compactor driven by a multi-stage air cylinder (665), as detailed further in FIG. 7, showing the a first, second and third piston of the device (710', 710", and 710''', respectively) that are connected to a singular internal shaft (730), where the pistons move along a linear axis and form a sealing interface against the cylinder housing (740). Further indicated are separation zones (720' and 720", respectively) within the cylinder housing (740). The end (750) of the singular internal shaft (730) is adapted to allow attachment of briquetting tooling (not shown here).

Also shown in FIG. 6B is a multi-stage air cylinder (665), as detailed further in FIG. 7, showing the a first, second and third piston of the device (710', 710", and 710''', respectively) that are connected to a singular internal shaft (730), where the pistons move along a linear axis and form a sealing interface against the cylinder housing (740). Further indicated are separation zones (720' and 720", respectively) within the cylinder housing (740). The end (750) of the singular internal shaft (730) is adapted to allow attachment of briquetting tooling (not shown here).

The briquetting part of the combined briquetting and cyclonic device according to the present invention is now further explained by referring to FIGS. 8 to 11, each showing schematically in a partly cut open perspective view exemplary details of the briquetting device.

Figure 8:
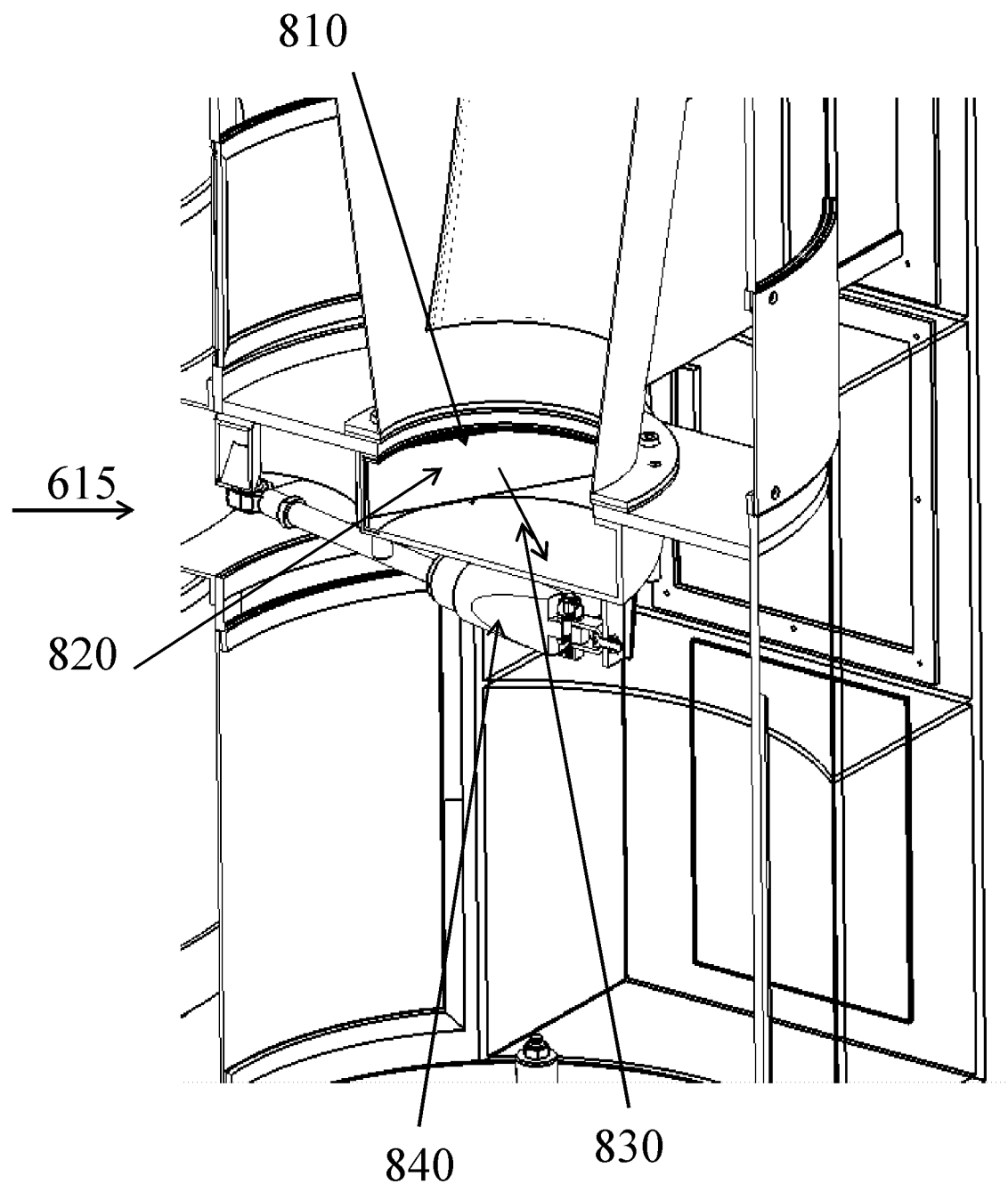
FIGS. 8 to 11 depict schematically details of the briquetting part of the process, which are suitable for the present invention.

Referring to FIG. 8, particles accumulated in the cyclone exit zone (810) fall into a collection zone of the briquetting device, which is essentially also a first pre-compaction zone, in which a pre-compaction tool e.g. a movable arm (820) moves along a first pre-compacting axis (830) to remove the accumulated particles from the collection zone and transport these to a further compaction zone, which may be a further pre-compaction zone or the final briquetting, whilst inducing a pre-compaction or pre-compression to reduce volume of the accumulated particles, such as dust, and increase density prior to the final briquetting process.

Figure 9:
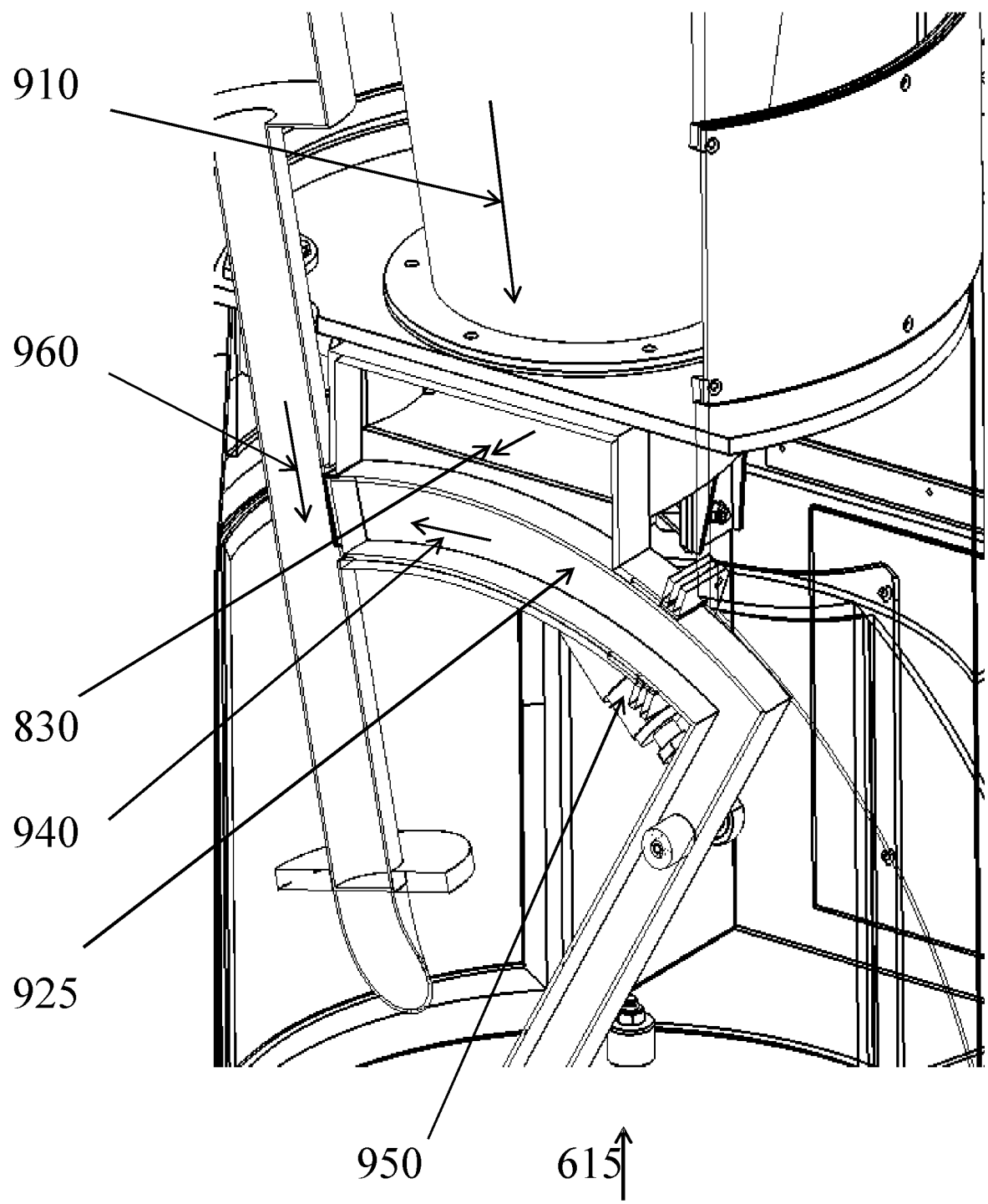
Figure 10:
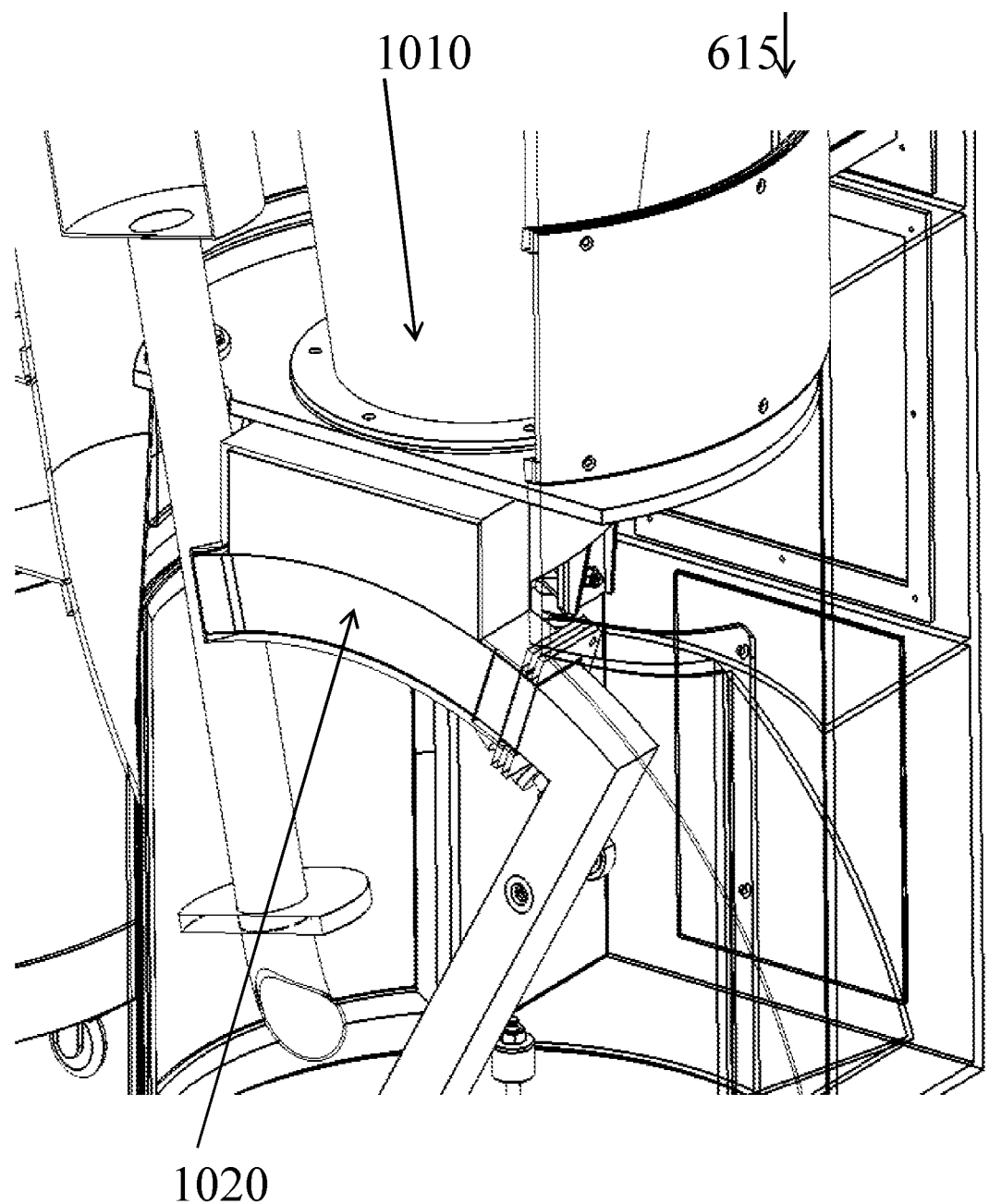
Figure 11:
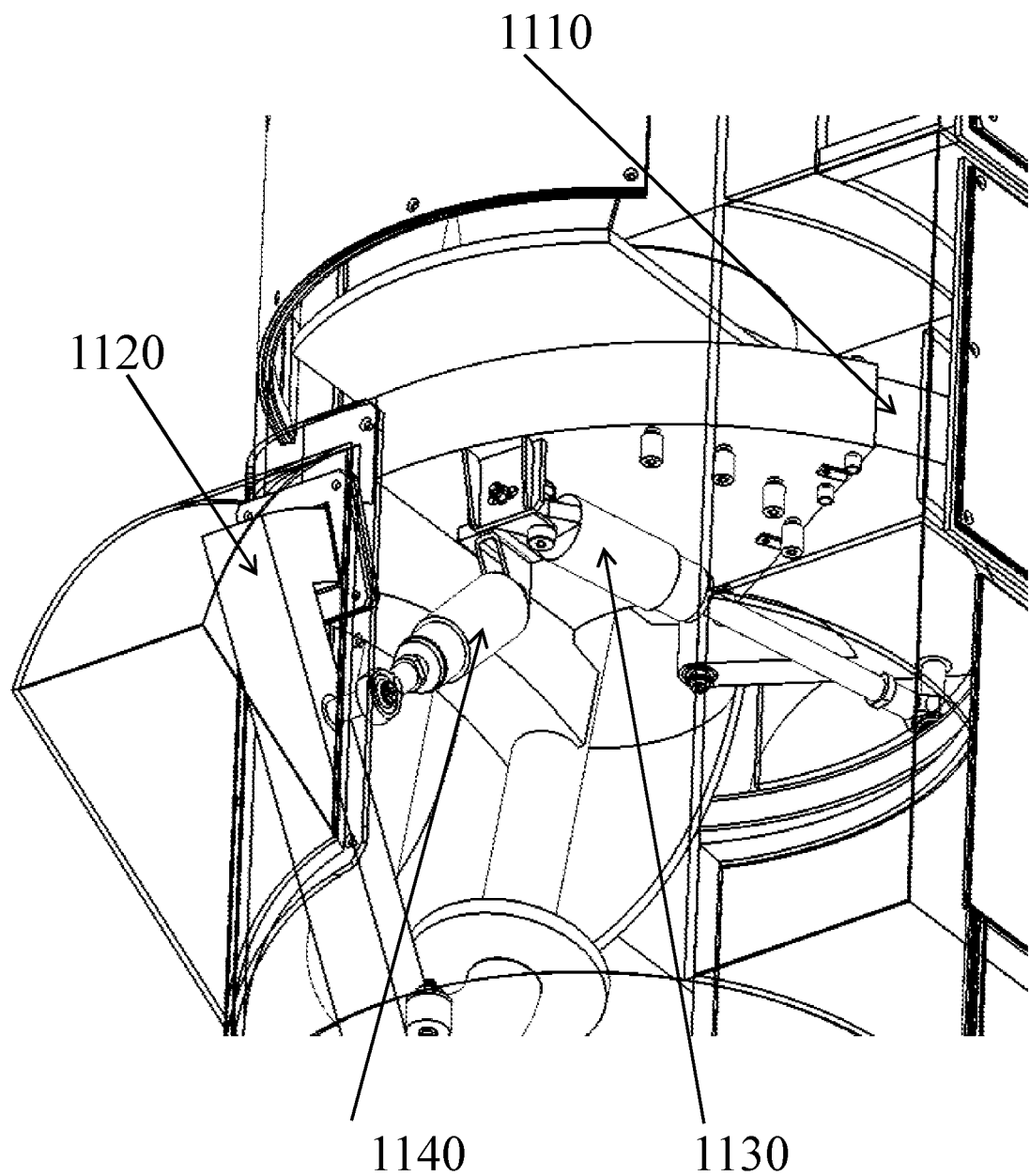

In FIG. 9, the accumulated particles of the pre-compression zone (925) are further transferred, such as by gravity, into a further collection zone along a first axis of motion (940) of the first transportation and pre-compaction stage. FIG. 9 depicts in further detail the briquetting part of the process as previously outlined, showing the zone (910) where the contaminants are removed from the cyclonic separation processes enter the briquetting device. A pre-compaction arm (820 in FIG. 8) is moved along an axis along the direction of the $1^{st}$ stage pre-compaction and transportation (920), such that the pre-compacted material reaches the $2^{nd}$ stage transportation and pre-compaction arm (925) which moves along the second stage compaction arm direction (940), when activated by air cylinder (950). From the $2^{nd}$ stage the material is moved towards a further pre-compaction stage, or as shown here, towards the high force final multistage compaction tool, moving along a final compacting direction (960). FIG. 10 depicts the same apparatus (615) as in FIG. 9 with accumulated particles exiting from the cyclone exit (1010), entering the first collection zone and then onto the second collection zone to be treated and further compacted by the $2^{nd}$ stage transportation and pre-compaction arm. 1020. As further shown in FIG. 11 accumulated particles exiting from the cyclone exit and being treated and further compacted by the $1^{st}$ stage transportation and pre-compaction arm (1110) depicts the $2^{nd}$ stage transportation and pre-compaction arm (1130). The first stage transportation and pre-compaction arm is driven by first stage drive cylinder (1130), whilst the second stage transportation and pre-compaction arm is driven by second stage drive (1140).

The final briquetting, high force final multistage compaction device required to make dense briquettes the high force final multistage compaction tool is moving along a final compacting direction (see FIG. 9, 960). In FIG. 6B, the single multi stage air cylinder device (665) is shown to create this force and an example of a multistage cylinder is depicted in FIG. 7 as described herein above and as an example of a multistage air cylinder. Assuming an air pressure of 90 PSI (620 kPa) a two-stage process can easily be operated. However, a higher number of stages could be executed, and this could range from 1-10 million stages and more likely from 2-20 stages and most likely between 8-12 stages.

With continued desire to increase operational efficiency, as part of this effort, staffing reductions is common in most manufacturing environments. Simply having the cyclone process running on its own is not ideal, whilst the addition of a sight glass at the base of the cyclone requires an operator to walk to the cyclone to inspect.

In order to increase operational efficiency and safety, new ways must be found to allow the reduced number of machine operators to interact with the process in a more efficient manner. Simply adding camera surveillance within the cyclone is problematic as space for such technology is limited, and lenses of such equipment become contaminated. Adding additional sensing equipment is also desired however similar problems exist.

Figure 12A:
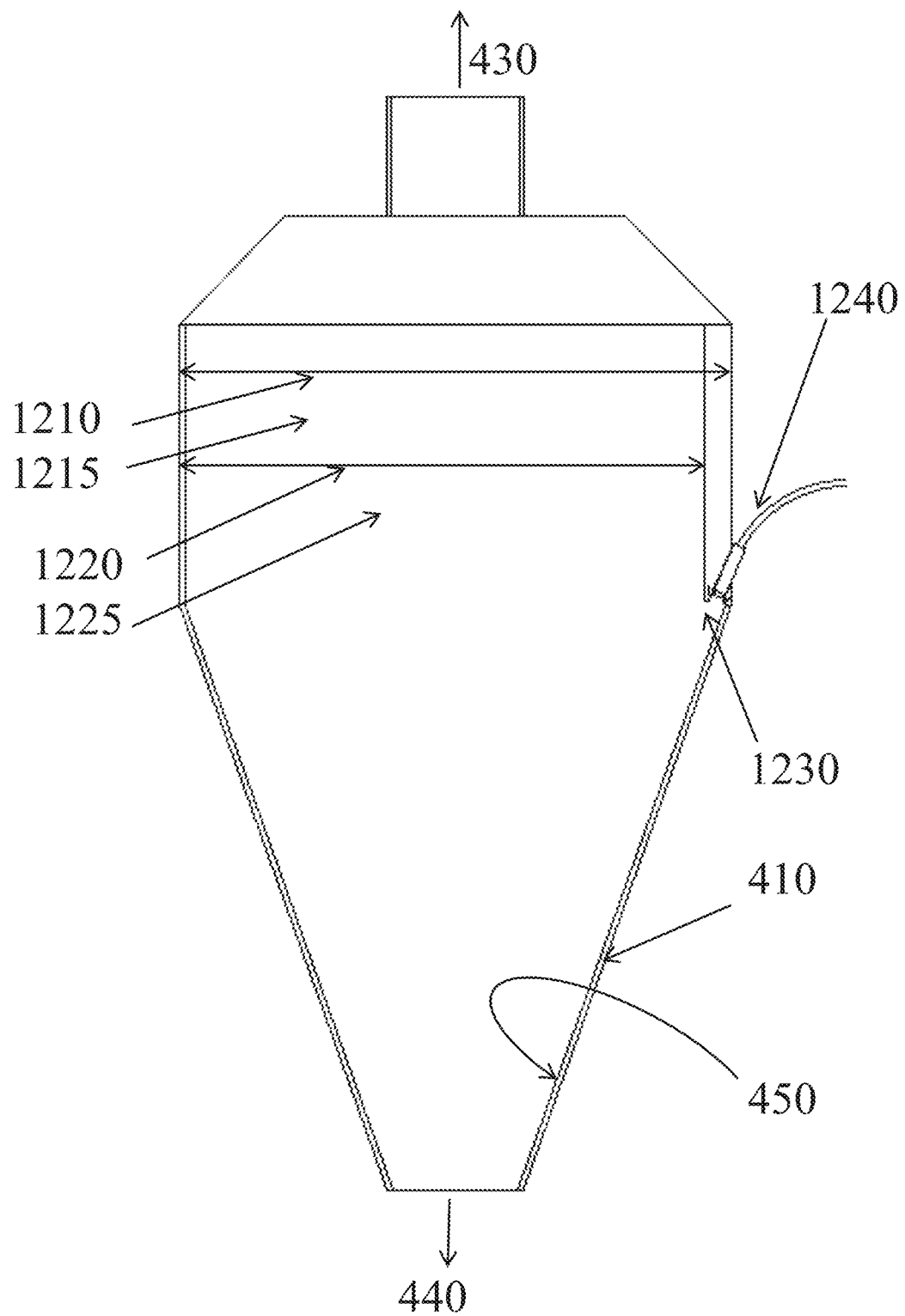
FIG. 12A depicts schematically a preferred execution of the present invention with a stepped housing of the cyclonic separator.
Figure 12B:
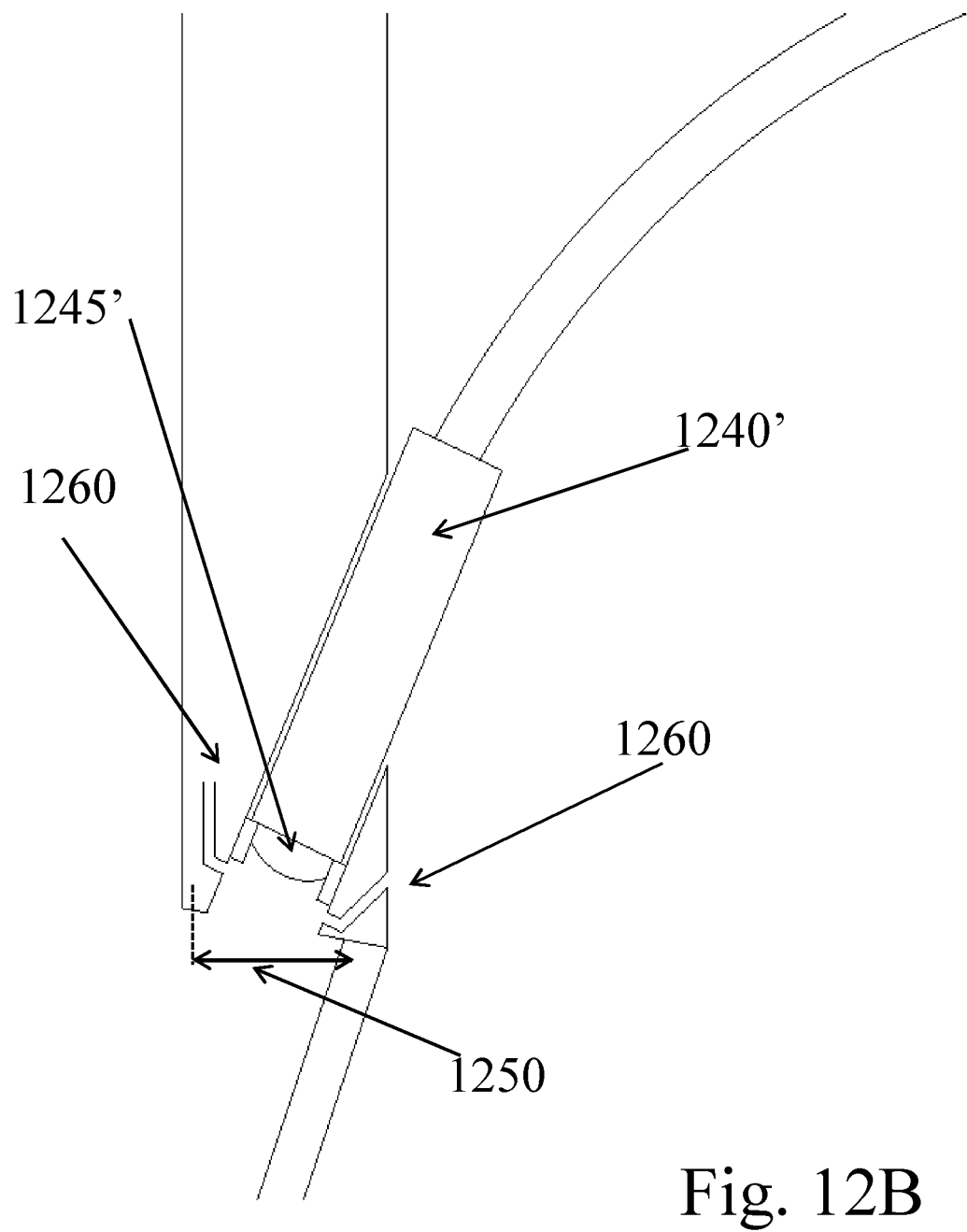
FIGS. 12B to D depict schematically preferred executions of the present invention, wherein sensing means are introduced in the stepped housing of a cyclonic separator.
Figure 12C:
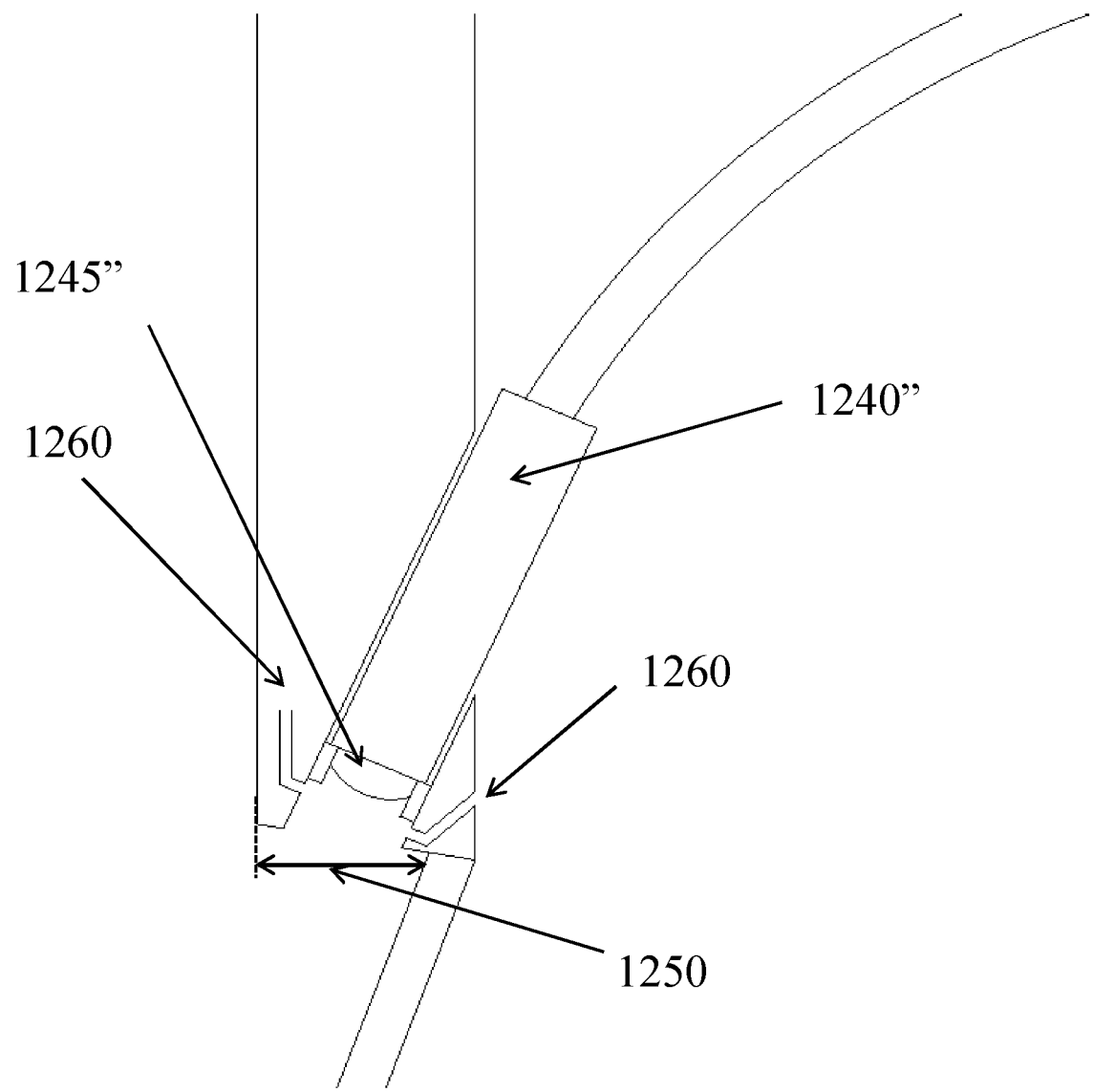
Figure 12D:
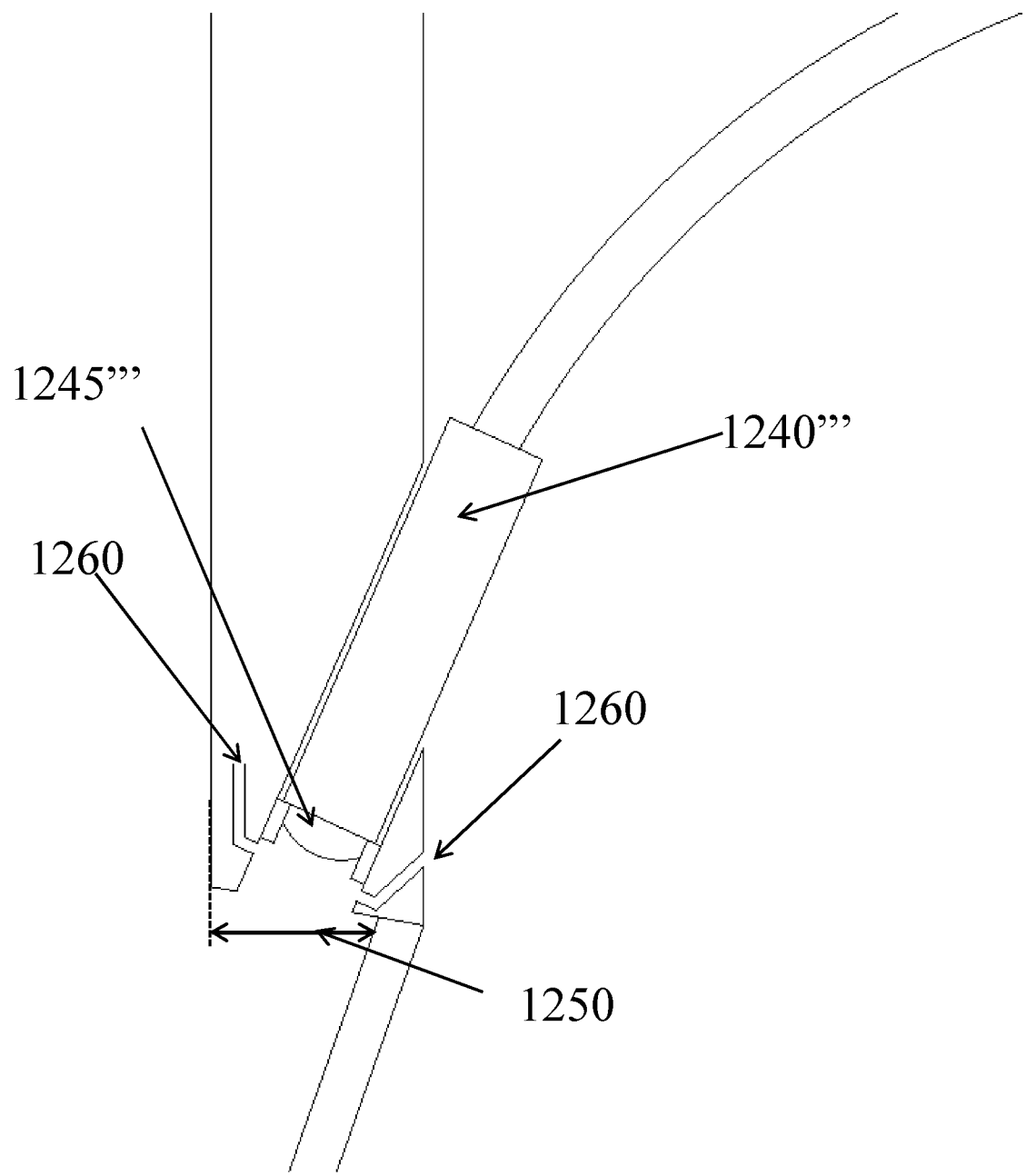

A solution to this aspect can be provided by a cyclone design as shown in FIG. 12A and particular executions of a sensing equipment in FIGS. 12B to D.

Therein a cyclonic separation device as outlined and described herein above (see FIGS. 4A and B) is shown with the body of the cyclonic separation processes (410). The outgoing clean fluid stream is leaving the cyclone at the upper exit (430), and the accumulated contaminants are removed from the cyclonic separation device from the lower exit zone (440). The contaminants slide against the inner cyclone side wall (450) after rotating in a vortex form which ultimately causes the contaminants to reduce velocity and fall out of the vortex. The cyclone body exhibits in its upper portion, i.e. at the part where the particle loaded air is entering the cyclone and which typically exhibits a cylindrical shape, a first section (1215) exhibiting a first diameter (1210) and a second section (1225) positioned more towards the lower exit zone (440) than the first section, which exhibits a slightly reduced diameter (1220). The two sections are arranged such that a step (1230) is created in the upper, typically cylindrical portion of the cyclone as a result of the differing diameters (1210 and 1220, respectively) and optionally non-concentric arrangement of the sections. Such a step may now very suitably be used to introduce devices (1240) such as lighting, camera, vision or, sensing systems.

FIGS. 12B to 12D depict exemplarily such devices in further detail, such as a video camera system (1240'), a sensing system (1240''), or a lighting system (1240''') e.g. to enhance a video camera system. Such devices fit into the step (1250) as the result of the differing diameters of the sections. Further, additional air may be introduced through air channels as a cleaning air jet system (1260) and blown towards the sensing surface (1245) of the devices (1240), such as onto the camera lens (1245') or lighting device surface (1245''), to keep these contaminants free.

In the following, exemplary calculations for various duct pressure loss and velocity pressure are listed to allow better understanding especially of the detrimental impact of duct length from the source of the particle loaded fluid stream to the separation means.

First, certain parameters have been kept identical for all Examples (See FIG. 4):

| Fluid type | | air | | |
|---|---|---|---|---|
| Duct type | | round | | |
| Duct diameter | [inches] | 3.93701 | [m] | 0.10 |
| (actual) Flow rate | [ACFM] | 295 | [m³/hr] | 680 |
| Viscosity | [cP] | 0.018 | | |
| Inlet pressure | [PSIG] | 0 | [Pa] | 0 |
| Temperature | [° F.] | 70 | [° C.] | 21.1 |
| Duct material | | galvanized Metal | | |
| Duct roughness | [ft] | 0.0005 | [mm] | 0.1524 |
| Fluid velocity | [ft/min] | 3491.26 | [m/sec] | 17.74 |
| Re-Number | [—] | 118308 | | |
| Flow region | | turbulent | | |
| Friction factor | [—] | 0.0235 | | |
| Density at inlet | [lbm/cft] | 0.075 | [kg/m³] | 1.20 |
| Specific fluid volume at inlet | | 13.34 | | |
| Specific heat ratio | | 1.4 | | |
| Velocity pressure | [inches water] | 0.761 | [Pa] | 190 |
| Hood entry type | None | | | |
| Duct exit configuration | | main duct line | | |
| Exit configuration loss | [inches water] | 0 | [Pa] | 0 |

Then for varying duct length, the total and the straight duct pressure loss have been determined (See FIG. 4):

Example A

| Duct length | [ft] | 279 | [m] | 85 |
|---|---|---|---|---|
| Total duct pressure loss | [inches water] | 15.532 | [Pa] | 3869 |
| Straight duct loss | [inches water] | 15.532 | [Pa] | 3869 |

Example B

| Duct length | [ft] | 65 | [m] | 19.81 |
|---|---|---|---|---|
| Total duct pressure loss | [inches water] | 3.565 | [Pa] | 888 |
| Straight duct loss | [inches water] | 3.565 | [Pa] | 888 |

Example C

| Duct length | [ft] | 0 | [m] | 0 |
|---|---|---|---|---|
| Total duct pressure loss | [inches water] | non-detectable | [Pa] | non-detectable |
| Straight duct loss | [inches water] | non-detectable | [Pa] | non-detectable |

This clearly demonstrates the benefits of positioning the separation and briquetting equipment as close to the source as possible, and the present invention provides a technically and commercially viable solution for this.

What is claimed is:

1. An equipment (600) for separating a plurality of particles from a fluid stream and briquetting said plurality of particles, said equipment comprising:
   a cyclonic separator (610) capable of accumulating particles of said plurality of particles loaded fluid in a particle outlet zone; and
   a particle compactor (615) capable of forming briquettes comprising one or more pre-compaction means and a final briquetting means;
   said particle compactor (615) being essentially unitary with a cyclonic separator by being directly connected thereto and being directly underneath said cyclonic separator along the direction of gravity; and
   said one or more pre-compaction means is a mechanical press compactor that comprises a multi stage air cylinder (665) adapted to be driven by pressurized air wherein said one or more pre-compaction means and said final briquetting means are actuated by said multi stage air cylinder.

2. The equipment according to claim 1, wherein at least one of said one or more pre-compaction means is a low air-pressure actuated mechanical press compactor.

3. The equipment according to claim 1, wherein said cyclonic separator and said one or more pre-compaction means are in an air-tight closed housing, optionally comprising a pressure sensor.

4. The equipment according to claim 3, wherein said step is adapted to receive a sensing means to allow surveillance and control of said cyclonic separator, said sensing means comprising one or more elements selected from the group consisting of a camera system, a lighting system, and a cleaning air jet system.

5. The equipment according to claim 1, wherein said cyclonic comprises a first section and second section positioned downwards towards said particle outlet zone,
   wherein said second section exhibits a diameter that is smaller than the diameter of said first section, and
   wherein said first section and said at least one further section are positioned such that a step is created in a wall of said cyclotronic separator.

6. A manufacturing equipment comprising equipment for separating a plurality of particles from a fluid stream and briquetting said plurality of particles according to claim 1.

7. A process for separating a plurality of particles from a particle loaded fluid stream and briquetting said plurality of particles, said process comprising the steps of:
   providing a stream of particle loaded liquid or gaseous fluid and air;
   accumulating a plurality of particles of said particle loaded fluid stream in a particle outlet zone for sending to a cyclonic separator (610);
   forming briquettes in a particle compactor (615) comprising one or more pre-compaction device(s), comprising a mechanical press compactor having a multi stage air cylinder, and a final briquetting device wherein said multi stage air cylinder is adapted to be driven by pressurized air wherein said one or more pre-compaction devices and said final briquetting device are actuated by said multi stage air cylinder;
   feeding said particle loaded fluid stream into a cyclonic separator (610);
   accumulating a plurality of particles in a particle accumulating zone of said cyclonic separator;
   transferring said accumulated plurality of particles through an outlet zone (810) of said cyclonic separator (610) directly to said particle compactor;
   submitting said plurality of particles to a pre-compacting step in said pre-compaction device(s);
   transferring said plurality of particles from said pre-compaction step to one or more further pre-compaction steps, and to said final briquetting step by employing no other transport means than said one or more pre-compaction devices;
   actuating said final briquetting device for forming a plurality of briquettes by said multi stage air cylinder that concurrently drives said one or more pre-compaction devices, and using pressurized air for actuating said multi stage air cylinder, wherein said pressurized air is less than 10 bar.

8. The process according to claim 7, wherein said plurality of particles of said particle loaded fluid stream exhibit differing properties selected from the group consisting of composition, size, and density.

9. The process according to claim 8, wherein said fluid particle loaded stream is air, and said plurality of particles result from a manufacturing process of hygiene articles, comprising particles selected from the group consisting of cellulose fibers, dust, and superabsorbent polymer particles.

10. The process according to claim 7, wherein said briquettes exhibit a size selected from the group consisting of less than 125 000 cm$^3$, less than 1000 cm$^3$, less than 1 cm$^3$ but more than 0.001 cm$^3$, and more than 0.008 cm$^3$.

11. A process according to claim 7, wherein said plurality of briquettes exhibit a density selected from the group consisting of more than 100 kg/m$^3$, more than 800 kg/m$^3$, and more than 1000 kg/m$^3$.

12. A manufacturing process comprising a process according to claim 7, further comprising the steps of:
- providing an automated briquette transport system, said automated briquette transport system being a continuous transport system, selected from the group consisting of a screw conveyor, a belt conveyor, a bucket conveyor, a pneumatic transfer conveyor, a vibrating conveyor, and a continuous flow conveyor;
- providing a briquette storage or disposal system selected from the group consisting of a plurality of bags exhibiting a volume of at least 100l, or more than 1 $m^3$, a plurality of drums that are moveable drums, a plurality of silos exhibiting a volume of more than 1 $m^3$, a storage space adapted to allow heaps of briquettes being formed, said heaps exhibiting a volume of 1 $m^3$, or more than 10 $m^3$, and a continuous transport system connected to a downstream processing step, said downstream processing step selected from the group consisting of thermal recuperation and waste treatment system; and
- transporting said briquettes by said transport system to said briquette storage or said disposal system.

* * * * *